United States Patent
Eidenschink et al.

(10) Patent No.: US 7,314,480 B2
(45) Date of Patent: *Jan. 1, 2008

(54) ROTATING BALLOON EXPANDABLE SHEATH BIFURCATION DELIVERY

(75) Inventors: Tracee Eidenschink, Wayzata, MN (US); The Thomas Trinh Tran, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/657,472

(22) Filed: Sep. 8, 2003

(65) Prior Publication Data

US 2004/0172121 A1  Sep. 2, 2004

Related U.S. Application Data

(63) Continuation-in-part of application No. 10/375,689, filed on Feb. 27, 2002.

(51) Int. Cl.
*A61F 2/06* (2006.01)
*A61M 29/00* (2006.01)

(52) U.S. Cl. .................. 623/1.11; 623/1.35; 604/103.05

(58) Field of Classification Search ............. 604/96.01, 604/101.01, 103, 103.03–103.05, 264; 606/108, 606/194; 623/1.11, 1.35
See application file for complete search history.

(56) References Cited

U.S. PATENT DOCUMENTS

| 4,448,195 A | 5/1984 | Leveen et al. ............ 128/344 |
| 4,484,585 A | 11/1984 | Baier ......................... 128/748 |
| 4,601,701 A | 7/1986 | Mueller, Jr. .................. 604/83 |
| 4,769,005 A | 9/1988 | Ginsburg et al. ............. 604/53 |
| 4,776,337 A | 10/1988 | Palmaz ....................... 128/343 |
| 4,913,141 A | 4/1990 | Hillstead .................... 606/108 |
| 4,994,071 A | 2/1991 | MacGregor ................. 606/194 |
| 4,998,923 A | 3/1991 | Samson et al. ............. 606/194 |
| 5,019,085 A | 5/1991 | Hillstead .................... 606/108 |

(Continued)

FOREIGN PATENT DOCUMENTS

DE  297 01 758  5/1997

(Continued)

OTHER PUBLICATIONS

Foley et al., "Bifurcation Lesion Stenting", *The Thoraxcentre Journal*, vol. 8, No. 4, (1996).

(Continued)

*Primary Examiner*—Kevin C. Sirmons
*Assistant Examiner*—Andrew Gilbert
(74) *Attorney, Agent, or Firm*—Merchant & Gould, P.C.

(57) ABSTRACT

A stent delivery assembly comprises a balloon catheter with a rotatable assembly disposed thereabout. The rotatable assembly comprises a rotatable sheath which in a reduced state is freely rotatable about the medical balloon and when in the expanded state is frictionally engaged by the expanded balloon. A secondary guide wire housing is at least partially engaged to the rotatable sheath. A stent may be disposed about at least a portion of the rotatable sheath and at least a portion of the secondary guide wire housing so that a distal end portion of the secondary guide wire housing exits the flow path of the stent through one of the plurality of cell openings which the stent defines.

25 Claims, 25 Drawing Sheets

U.S. PATENT DOCUMENTS

| | | | |
|---|---|---|---|
| 5,120,308 A | 6/1992 | Hess | 604/95 |
| 5,122,154 A | 6/1992 | Rhodes | 606/198 |
| 5,195,984 A | 3/1993 | Schatz | 606/195 |
| 5,219,355 A | 6/1993 | Parodi et al. | 606/191 |
| 5,316,023 A | 5/1994 | Palmaz et al. | 128/898 |
| 5,380,299 A | 1/1995 | Fearnot et al. | |
| 5,397,305 A | 3/1995 | Kawula et al. | 604/96 |
| 5,449,343 A | 9/1995 | Samson et al. | 604/96 |
| 5,449,382 A * | 9/1995 | Dayton | 623/1.15 |
| 5,477,856 A | 12/1995 | Lundquist | 128/642 |
| 5,556,413 A | 9/1996 | Lam | |
| 5,571,086 A | 11/1996 | Kaplan et al. | |
| 5,609,627 A | 3/1997 | Goicoechea et al. | 623/1 |
| 5,632,763 A | 5/1997 | Glastra | 606/194 |
| 5,643,278 A | 7/1997 | Wijay | 606/108 |
| 5,670,161 A | 9/1997 | Healy et al. | |
| 5,683,345 A | 11/1997 | Waksman et al. | 600/3 |
| 5,697,971 A | 12/1997 | Fischell et al. | 623/1 |
| 5,725,519 A | 3/1998 | Penner et al. | 606/1 |
| 5,744,515 A | 4/1998 | Clapper | |
| 5,749,825 A | 5/1998 | Fischell et al. | 600/3 |
| 5,755,734 A | 5/1998 | Richter et al. | 606/194 |
| 5,755,735 A | 5/1998 | Richter et al. | 606/194 |
| 5,755,778 A | 5/1998 | Kleshinski | 623/1 |
| 5,772,669 A | 6/1998 | Vrba | 606/108 |
| 5,776,141 A | 7/1998 | Klein et al. | |
| 5,797,952 A | 8/1998 | Klein | 606/198 |
| 5,817,100 A * | 10/1998 | Igaki | 623/1.11 |
| 5,824,055 A | 10/1998 | Spiridigliozzi et al. | 623/1 |
| 5,836,952 A | 11/1998 | Davis et al. | |
| 5,843,027 A * | 12/1998 | Stone et al. | 604/509 |
| 5,873,906 A | 2/1999 | Lau et al. | 623/1 |
| 5,876,374 A | 3/1999 | Alba et al. | 604/96 |
| 5,893,868 A | 4/1999 | Hanson et al. | 623/1.11 |
| 5,906,640 A | 5/1999 | Penn et al. | 623/1 |
| 5,908,405 A | 6/1999 | Imran et al. | 604/53 |
| 5,921,995 A | 7/1999 | Kleshinski | 606/153 |
| 5,935,161 A | 8/1999 | Robinson et al. | 623/1 |
| 5,941,908 A | 8/1999 | Goldsteen et al. | 623/1 |
| 5,951,569 A | 9/1999 | Tuckey et al. | 606/108 |
| 5,957,929 A | 9/1999 | Brenneman | 606/108 |
| 5,961,546 A | 10/1999 | Robinson et al. | 623/1 |
| 5,961,548 A | 10/1999 | Shmulewitz | 623/1 |
| 6,013,092 A | 1/2000 | Dehdashtian et al. | 606/194 |
| 6,015,424 A | 1/2000 | Rosenbluth et al. | |
| 6,017,362 A | 1/2000 | Lau | 623/1 |
| 6,027,460 A | 2/2000 | Shturman | 600/585 |
| 6,033,434 A | 3/2000 | Borghi | 623/1 |
| 6,048,350 A | 4/2000 | Vrba | |
| 6,048,361 A | 4/2000 | Von Oepen | 623/1 |
| 6,056,722 A | 5/2000 | Jayaraman | 604/102 |
| 6,056,775 A * | 5/2000 | Borghi et al. | 623/1.16 |
| 6,059,813 A | 5/2000 | Vrba et al. | 606/198 |
| 6,071,286 A | 6/2000 | Mawad | 606/108 |
| 6,077,297 A | 6/2000 | Robinson et al. | 623/1.11 |
| 6,090,127 A | 7/2000 | Globerman | 606/194 |
| 6,096,073 A | 8/2000 | Webster et al. | 623/1.16 |
| 6,099,497 A * | 8/2000 | Adams et al. | 604/96.01 |
| 6,110,191 A | 8/2000 | Dehdashtian et al. | 606/192 |
| 6,117,156 A | 9/2000 | Richter et al. | 606/194 |
| 6,120,522 A | 9/2000 | Vrba et al. | 606/190 |
| 6,132,450 A | 10/2000 | Hanson et al. | 606/198 |
| 6,143,014 A | 11/2000 | Dehdashtian et al. | 606/192 |
| 6,146,415 A | 11/2000 | Fitz | 623/1.11 |
| 6,152,944 A | 11/2000 | Holman et al. | 623/1.11 |
| 6,165,195 A * | 12/2000 | Wilson et al. | 606/194 |
| 6,165,210 A | 12/2000 | Lau et al. | 623/1.12 |
| 6,187,015 B1 | 2/2001 | Brenneman | 606/108 |
| 6,190,360 B1 | 2/2001 | Iancea et al. | 604/164.09 |
| 6,190,393 B1 | 2/2001 | Bevier et al. | 606/108 |
| 6,210,380 B1 | 4/2001 | Mauch | 604/284 |
| 6,210,431 B1 | 4/2001 | Power | 623/1.11 |
| 6,221,090 B1 | 4/2001 | Wilson | 606/194 |
| 6,221,097 B1 | 4/2001 | Wang et al. | 623/1.11 |
| 6,224,587 B1 | 5/2001 | Gibson | 604/528 |
| 6,238,410 B1 | 5/2001 | Vrba et al. | 606/198 |
| 6,246,914 B1 | 6/2001 | De la Rama et al. | 607/122 |
| 6,254,593 B1 | 7/2001 | Wilson | 606/1.11 |
| 6,258,052 B1 | 7/2001 | Milo | 604/22 |
| 6,258,073 B1 | 7/2001 | Mauch | 604/284 |
| 6,264,688 B1 | 7/2001 | Herklotz et al. | 623/1.16 |
| 6,280,466 B1 | 8/2001 | Kugler et al. | 623/1.12 |
| 6,287,277 B1 | 9/2001 | Yan | 604/96.01 |
| 6,287,330 B1 | 9/2001 | Johansson et al. | 623/1.13 |
| 6,290,673 B1 | 9/2001 | Shanley | 604/102.02 |
| 6,299,636 B1 | 10/2001 | Schmitt et al. | 623/1.2 |
| 6,302,906 B1 | 10/2001 | Goicoechea et al. | 623/1.11 |
| 6,319,275 B1 | 11/2001 | Lashinski et al. | 623/1.11 |
| 6,322,548 B1 | 11/2001 | Payne et al. | 604/500 |
| 6,350,278 B1 | 2/2002 | Lenker et al. | |
| 6,361,544 B1 | 3/2002 | Wilson et al. | 606/194 |
| 6,361,555 B1 | 3/2002 | Wilson | 623/1.11 |
| 6,364,893 B1 | 4/2002 | Sahatjian et al. | 606/194 |
| 6,371,978 B1 | 4/2002 | Wilson | 623/1.11 |
| 6,375,660 B1 | 4/2002 | Fischell et al. | 606/108 |
| 6,379,372 B1 | 4/2002 | Dehdashtian et al. | 606/192 |
| 6,387,120 B2 | 5/2002 | Wilson et al. | 623/1.11 |
| 6,391,050 B1 | 5/2002 | Broome | 623/1.11 |
| 6,406,487 B2 | 6/2002 | Brenneman | 623/1.11 |
| 6,406,489 B1 | 6/2002 | Richter et al. | 623/1.16 |
| 6,416,529 B1 | 7/2002 | Holman et al. | 606/194 |
| 6,436,104 B2 | 8/2002 | Hojeibane | 606/108 |
| 6,443,980 B1 | 9/2002 | Wang et al. | 623/1.11 |
| 6,471,672 B1 | 10/2002 | Brown et al. | |
| 6,475,166 B1 | 11/2002 | Escano | 600/585 |
| 6,482,211 B1 | 11/2002 | Choi | 606/108 |
| 6,488,694 B1 | 12/2002 | Lau et al. | 606/194 |
| 6,508,835 B1 | 1/2003 | Shaolian et al. | 623/1.35 |
| 6,514,281 B1 | 2/2003 | Blaeser et al. | 623/1.12 |
| 6,520,983 B1 | 2/2003 | Colgan et al. | 623/1.11 |
| 6,520,988 B1 | 2/2003 | Colombo et al. | 623/1.35 |
| 6,530,947 B1 | 3/2003 | Euteneuer et al. | 623/1.11 |
| 6,533,805 B1 | 3/2003 | Jervis | 623/1.11 |
| 6,540,719 B2 | 4/2003 | Bigus et al. | 604/96.01 |
| 6,554,841 B1 | 4/2003 | Yang | 606/108 |
| 6,569,180 B1 | 5/2003 | Sirhan et al. | |
| 6,582,459 B1 | 6/2003 | Lau et al. | 623/1.11 |
| 6,589,262 B1 | 7/2003 | Honebrink et al. | 606/191 |
| 6,596,020 B2 | 7/2003 | Vardi et al. | 623/1.11 |
| 6,599,315 B2 | 7/2003 | Wilson | 623/1.11 |
| 6,602,226 B1 | 8/2003 | Smith et al. | 604/103.05 |
| 6,607,506 B2 | 8/2003 | Kletschka | 604/96.01 |
| 6,613,067 B1 | 9/2003 | Johnson | 606/194 |
| 6,629,981 B2 | 10/2003 | Bui et al. | 606/108 |
| 6,660,030 B2 | 12/2003 | Shaolian et al. | |
| 6,669,718 B2 | 12/2003 | Besselink | 623/1.11 |
| 6,692,483 B2 | 2/2004 | Vardi et al. | |
| 2001/0049548 A1 | 12/2001 | Vardi et al. | 623/1.11 |
| 2002/0019664 A1 | 2/2002 | Douglas | 623/1.35 |
| 2002/0019665 A1 | 2/2002 | Dehdashtian et al. | 623/1.35 |
| 2002/0022874 A1 | 2/2002 | Wilson | 623/1.11 |
| 2002/0038140 A1 | 3/2002 | Yang et al. | |
| 2002/0038141 A1 | 3/2002 | Yang et al. | |
| 2002/0052640 A1 | 5/2002 | Bigus et al. | |
| 2002/0072755 A1 | 6/2002 | Bigus et al. | 606/108 |
| 2002/0111675 A1 | 8/2002 | Wilson | 623/1.35 |
| 2002/0116045 A1 | 8/2002 | Eidenschink | |
| 2002/0120320 A1 | 8/2002 | Wang et al. | |
| 2002/0165598 A1 | 11/2002 | Wahr et al. | |
| 2003/0023298 A1 | 1/2003 | Jervis | |
| 2003/0055483 A1 | 3/2003 | Gumm | 623/1.11 |
| 2003/0055484 A1 | 3/2003 | Lau et al. | 623/1.13 |
| 2003/0130716 A1 | 7/2003 | Weber et al. | 623/1.11 |
| 2003/0181923 A1 | 9/2003 | Vardi | |

| | | | |
|---|---|---|---|
| 2003/0195546 A1 | 10/2003 | Solar et al. | 606/192 |
| 2004/0172119 A1* | 9/2004 | Eidenschink | 623/1.11 |
| 2005/0149161 A1* | 7/2005 | Eidenschink et al. | 623/1.11 |
| 2005/0154442 A1* | 7/2005 | Eidenschink et al. | 623/1.11 |
| 2005/0273149 A1* | 12/2005 | Tran et al. | 623/1.11 |

FOREIGN PATENT DOCUMENTS

| | | |
|---|---|---|
| FR | 2 678 508 A1 | 1/1993 |
| WO | 00/44307 | 8/2000 |
| WO | 03/017872 | 3/2003 |
| WO | 03/017872 A1 | 3/2003 |
| WO | 03/055414 | 7/2003 |
| WO | WO 03/061529 A1 | 7/2003 |
| WO | WO 2004/075792 A1 | 9/2004 |

OTHER PUBLICATIONS

Schampaert, MD, Erick et al., "The V-Stent: A Novel Technique for Coronary Bifurcation Stenting", *Catheterization and Cardiovascular Diagnosis*, 39:320-326 (1996).

Pomerantz, MD, et al., "Distortion of Palmaz-Schatz Stent Geometry Following Side-Branch Balloon Dilation Through the Stent in a Rabbit Model", *Catheterization and Cardiovascular Diagnosis*, 40:422-426 (1997).

Palmaz, MD, et al., "Aortic Bifurcation Stenosis: Treatment with Intravascular Stents", *Journal of Vascular and Interventional Radiology*, vol. 2, No. 3, pp. 319-323 (Aug. 1991).

Oda, MD., et al., "Fork Stenting for Bifurcational Lesion", Journal of Interventional Cardiology, vol. 9, No. 6, pp. 445-454 (Dec. 1996).

Nakamura et al., "Techniques for Palmaz-Schatz Stent Deployment in Lesions With a Large Side Branch", Catheterization and Cardiovascular Diagnosis, vol. 34, pp. 353-361 (1995).

U.S. Appl. No. 10/747,546, filed Dec. 29, 2003, Eidenschink et al.

U.S. Appl. No. 10/757,646, filed Jan. 13, 2004, Eidenschink et al.

U.S. Appl. No. 10/780,937, filed Feb. 18, 2004, Eidenschink et al.

U.S. Appl. No. 10/784,337, filed Feb. 23, 2004, Eidenschink et al.

U.S. Appl. No. 10/863,724, filed Jun. 8, 2004, Eidenschink et al.

U.S. Appl. No. 10/375,689, filed Feb. 27, 2003, Eidenschink, Tracee.

Noveon, www.estane.com, Medical Urethanes Overview, 9 pages.

* cited by examiner

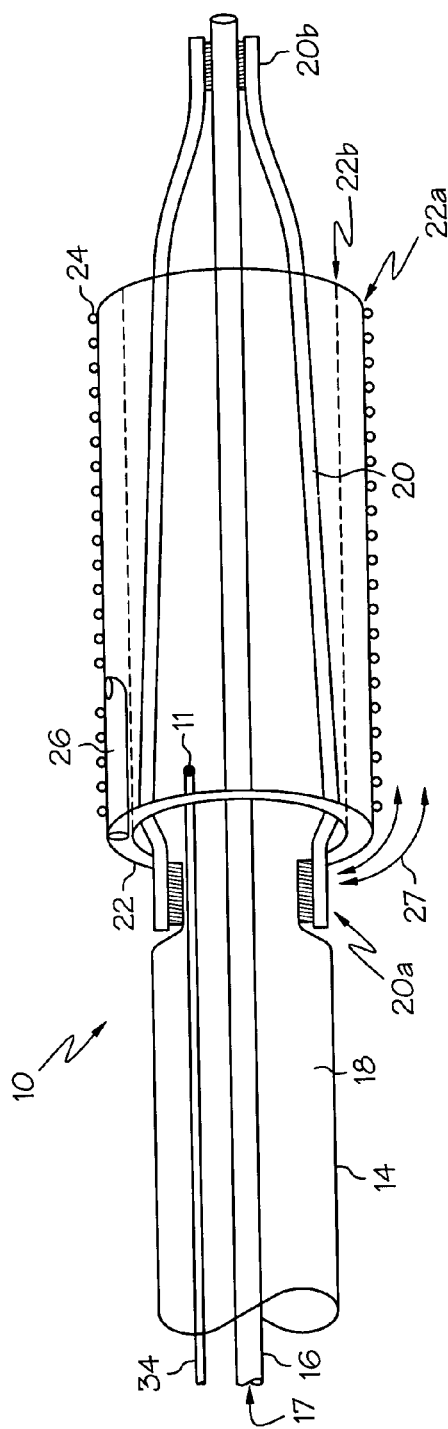
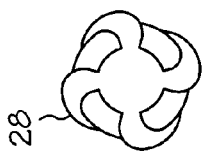
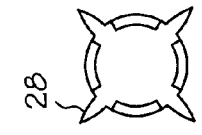
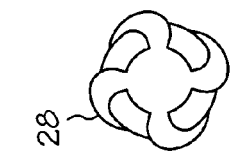
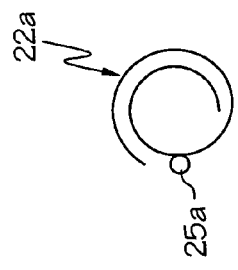

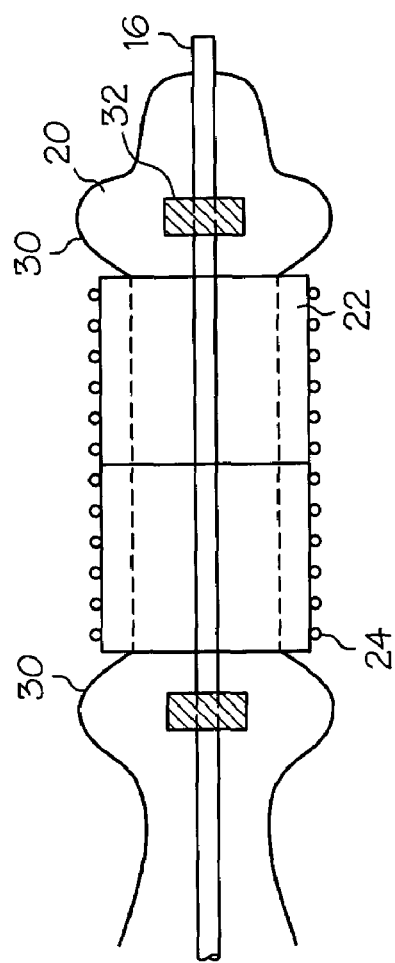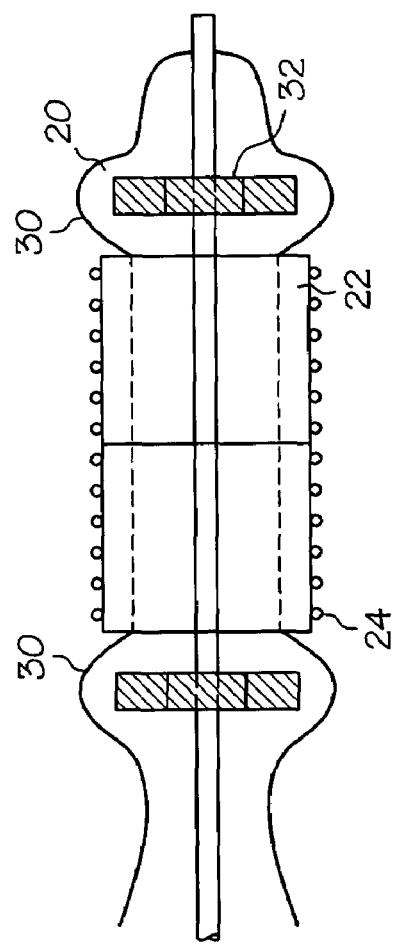

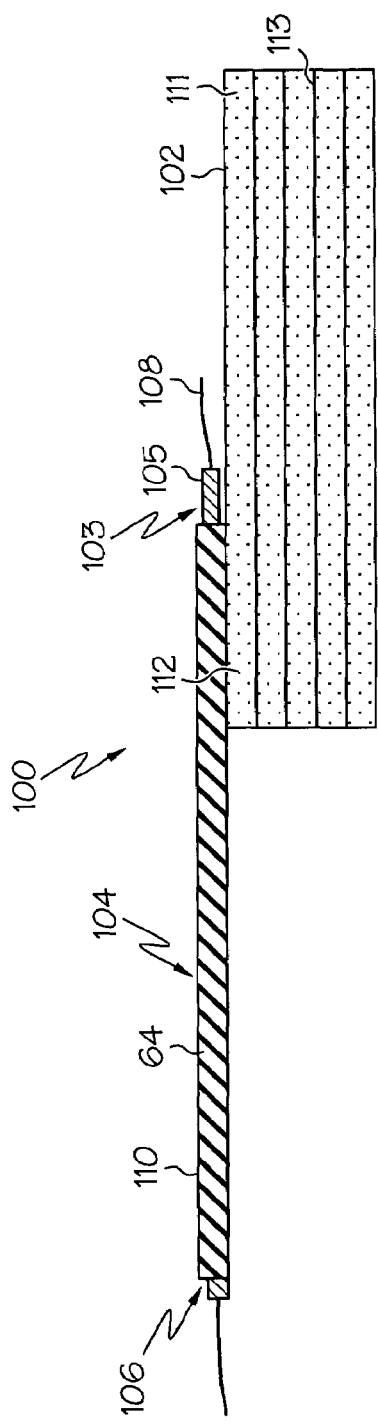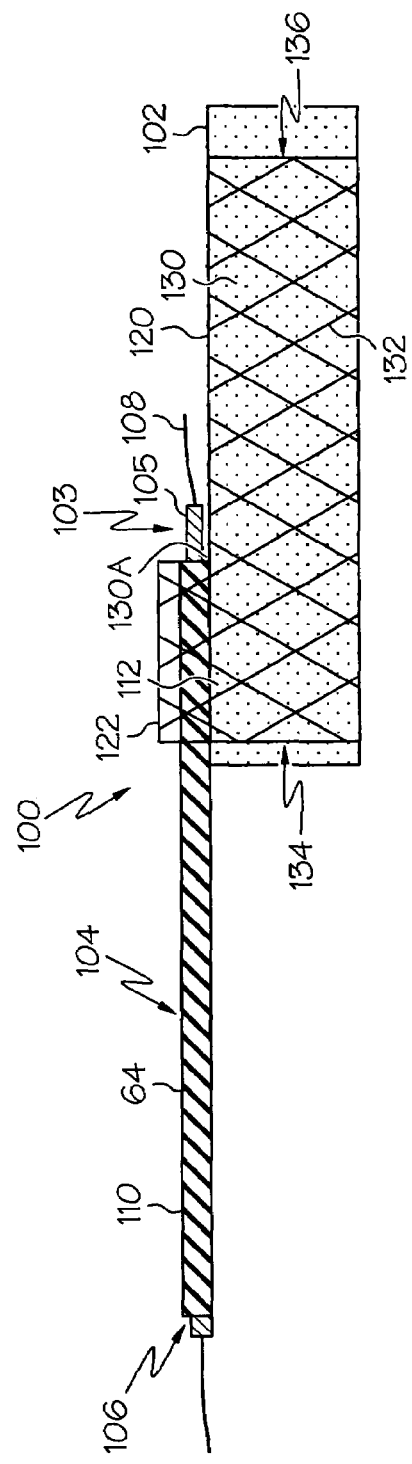

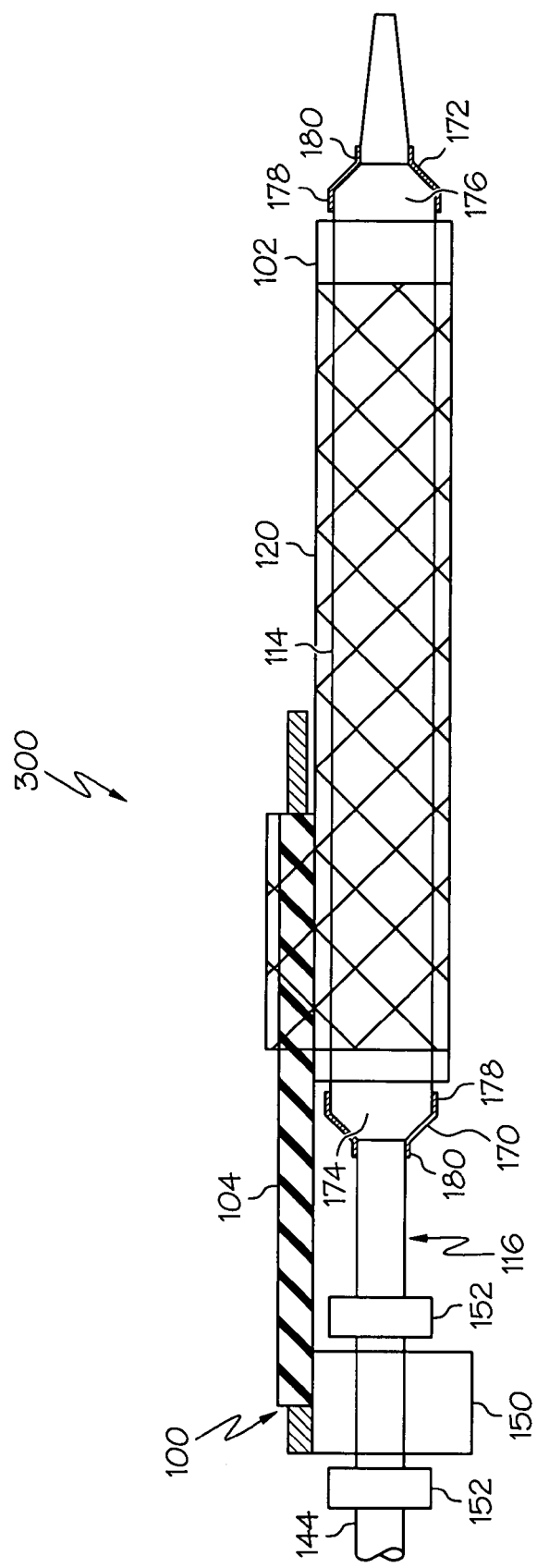

ROTATING BALLOON EXPANDABLE SHEATH BIFURCATION DELIVERY

CROSS-REFERENCE TO RELATED APPLICATIONS

This Application is a continuation-in-part (CIP) of Ser. No. 10/375,689, filed Feb. 27, 2003, the entire content of which is incorporated herein by reference.

STATEMENT REGARDING FEDERALLY SPONSORED RESEARCH

Not Applicable

BACKGROUND OF THE INVENTION

DESCRIPTION OF THE RELATED ART

Catheter systems such as angioplasty catheters, and stent delivery systems, as well as the stents associated therewith, are widely used in the treatment of stenoses, aneurysms, lesions, and other abnormalities within blood vessels and other body lumens. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

Treatment at bifurcation sites has been difficult. Although efforts have been made to use a stent at bifurcations, these sites have previously been problematic to treat. The specialty stents designed for bifurcations generally need specific alignment, radially as well as longitudinally. For example, U.S. Pat. No. 5,749,825 is representative of a catheter system that is intended to treat stenoses at an arterial bifurcation. The disclosure of U.S. Pat. No. 5,749,825 is hereby incorporated by reference.

A stent delivery system employing a stent assembly with branches intended for deployment in the adjacent branches of a vessel bifurcation has been proposed to allow placement of a portion of the assembly in both a primary passage, such as an artery, and a secondary passage, such as a side branch artery. Additionally, these stents generally have an opening which allows for unimpeded blood flow into the side branch artery. However, problems are still encountered in orienting the stent relative to the side branch at the bifurcation of the primary and secondary passages. Moreover, such bifurcated assemblies are typically specially manufactured at an increased cost over a more standard stent intended for single vessel deployment.

In delivering a stent to a vessel location, many current devices rely on either passive torque (e.g., pushing the stent forward and allowing the stent that is fixed on the guide wire/balloon to passively rotate itself into place) or creating torque from outside of the patient to properly orient the medical device in the passage. These devices and methods of achieving proper angular orientation have not been shown to be effective in properly placing and positioning the stent. As will be appreciated and understood by those skilled in the art, improper placement of the stent with respect to its rotational or circumferential orientation, or its longitudinal placement, could lead to obstruction of the side branch passage. It is important to properly position or center an opening formed in the bifurcated stent with the secondary passage to maximize flow therethrough.

Thus, a need exists for effectively treating stenosed passage bifurcations. This need includes more precise and exact longitudinal placement and rotational/circumferential orientation of the stent. A need also exists to provide a method and apparatus for using a standard so-called "single vessel" at a vessel bifurcation without the need of additional components of a specially designed bifurcated stent assembly. Furthermore a need exists to provide an existing stent delivery catheter with a mechanism that will allow the system to be retrofitted for use in bifurcated stent procedures.

Many commercially available devices do not maintain side branch access at the time of stent deployment. This results in the potential for plaque shift and occlusion of the secondary passage.

It would also be advantageous if stents could be placed across the side branch while wire position is maintained thereby helping to protect and secure further access to the side branch.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Some embodiments of the present invention include a freely rotating deployment assembly for a stent assembly for maintaining side branch access and protection.

In at least one embodiment the present invention contemplates an apparatus and method that improves the orientation of a stent by providing a more exact placement of the stent relative to the side branch passage. This, in turn, may lead to better protection of the side branch passage.

At least one embodiment of the invention includes a medical device with a balloon catheter shaft and a rotating sheath. The sheath is disposed about at least a portion of the balloon and is rotatable thereabout. Prior to delivery, at least a portion of a stent is disposed about the sheath. In some embodiments a secondary lumen is engaged to the sheath, a secondary guide wire may pass through the secondary lumen to provide rotational torque necessary for aligning a secondary opening and/or branch of the stent with a secondary vessel at a bifurcation site.

In at least one embodiment a rotating collar is disposed about a portion of the balloon catheter shaft proximal of the balloon. A proximal portion of the secondary lumen is engaged to the rotating collar.

In some embodiments the catheter shaft has a first guide wire lumen therethrough and an inflation lumen extending from a proximal region of the catheter shaft to a distal region of the catheter shaft.

In some embodiments no portion of the sheath is more than about 5 centimeters proximal to the most proximal portion of the balloon.

In some embodiments the stent is self expanding. In some embodiments the stent is balloon expandable.

In some embodiments the stent is made of shape memory material.

In some embodiments the stent defines a secondary opening through which the secondary guide wire is passed. In at least some embodiments the secondary opening is a cell opening in the wall of a "single vessel" stent. In some embodiments the cell opening or secondary opening is enlarged to better accommodate the passage of the secondary guide wire and/or to provide a more anatomically correct opening for the side vessel. In at least one embodiment the secondary opening is sized such that after delivery of the stent a secondary stent, in a pre-delivery state may be advanced therethrough into the side vessel. In at least one embodiment a portion of the secondary stent, in a deployed state is engaged to the primary stent within the secondary opening. In at least one embodiment one or more balloons may be utilized to seat or otherwise expand the primary stent at the vessel bifurcation.

In some embodiments the sheath is constructed such that it is radially expandable.

In some embodiments the sheath is constructed such that the stent may be crimped onto the sheath while permitting rotation of the sheath about the balloon.

In some embodiments the sheath is constructed of at least one homogeneous layer.

In some other embodiments the sheath has a low friction inner surface. In other embodiments a friction reducing substance is placed between the sheath and the inner balloon. In other embodiments a friction reducing substance is placed between an outer balloon and the inner balloon.

In some embodiments the sheath is constructed of a soft durometer polymer.

In at least one embodiment the sheath is constructed of multiple layers.

In at least one embodiment at least one of the layers is constructed of a first material having different properties from a second material found in at least one other layer.

In some other embodiments an inner layer constructed of a low friction material is in contact with the balloon. Materials such as PTFE and HDPE are used in some embodiments.

In some embodiments an outer layer of a soft durometer polymer suitable for securing the stent to the sheath is used.

In some other embodiments the sheath is made of a shape memory material so it shrinks back down for withdrawal.

In some other embodiments the sheath rotates freely.

In at least one other embodiment the longitudinal movement of the sheath relative to the balloon catheter shaft is limited with a safety tether. The safety tether can be a pull wire outside either guide wire lumen or it can be inside the second wire lumen. In some embodiments the rotating collar is adjacent to and/or between one or more locks or hubs along the catheter shaft to limit or prevent longitudinal displacement of the collar and and/or sheath. In at least one embodiment the hubs are comprise a hinged lock which may be positioned about an existing catheter shaft.

In at least one embodiment the catheter further comprises a balloon protector which is fitted over the balloon after the sheath and stent have been positioned thereabout in order to maintain the balloon in a folded and/or reduced diameter pre-delivery configuration. In at least one embodiment the protector is disposed about the proximal end and distal end of the balloon. In at least one embodiment, at least a portion of the protector defines a slit or longitudinal opening which allows the portion to be pealed or otherwise removed from the catheter prior to delivery.

In some embodiments the catheter balloon has at least one balloon cone distally offset from the distal most portion of the sheath or proximally offset from the proximal most portion of the sheath.

In some embodiments the assembly has marker bands located about the balloon catheter shaft. In some embodiments the marker bands have a greater diameter than the cross-sectional diameter of the sheath thereby limiting longitudinal movement of the sheath relative to the balloon catheter shaft. In some embodiments at least one marker band has a radiopaque portion.

In some embodiments a rotating collar is positioned about the second wire lumen and the balloon catheter shaft. In other such embodiments a first longitudinal lock is positioned about the second wire lumen and proximal to the rotating collar, and a second longitudinal lock is positioned about the balloon catheter shaft and distal to the rotating collar such that the longitudinal position of the sheath and collar is maintained.

In some embodiments the secondary lumen comprises a reinforcing member, such as a polymer tube of pebax, peek, polyimide, etc., a braided tube of metal wire or other material, a hypotube, or other device engaged to the sheath and engaged to the collar.

In some embodiments the hypotube is spiral cut. In some embodiments the hypotube comprises stainless steel. In some embodiments the hypotube comprises a polymer.

In some embodiments the proximal end of the hypotube is disposed in a second guide wire lumen of the collar.

In some embodiments the proximal end of the hypotube is engaged to an outside surface of the collar.

In some embodiments the sheath has a length that is substantially the same as the length of the catheter balloon.

In some embodiments the sheath comprises a secondary sheath opening for passage of the secondary guide wire therethrough. Where the sheath defines a secondary sheath opening, the sheath is further disposed about a portion of the secondary lumen. In at least one embodiment the secondary lumen interfaces with a portion of the balloon tangentially.

In some embodiments a secondary lumen and a secondary guide wire lumen are distinct from one another. In at least one embodiment, one or both of the secondary inflation lumen and the secondary guide wire lumen are provided with a substantially crescent shape which substantially corresponds to the curvature of the catheter shaft.

In some embodiments the balloon has a body portion with a cone portion distal to the body portion and a cone portion proximal to the body portion, and the sheath is disposed about the body portion and has a length substantially the same as the length of the body portion of the catheter balloon.

In some embodiments the length of the sheath is no greater than 2 centimeters longer than the length of the balloon.

In some embodiments the sheath extends distally from a location proximal to the proximal end of the catheter balloon. In some embodiments the sheath extends distally from a location equal to or less than 2 centimeters proximal to the proximal end of the catheter balloon.

In some embodiments the assembly provides for proper orientation relative to the side branch, side branch protection with the guide wire during stent deployment, proper placement of the stent both longitudinally and circumferentially, and reduction in the incidence of tangled wires which limits catheter advancement.

In other embodiments an outer balloon may replace the sheath of the above embodiments. The outer balloon in such instances may have the same qualities as the sheath as described in the embodiments above.

In at least one embodiment the secondary lumen further comprises a secondary inflation lumen and the catheter further comprises a secondary balloon. In at least one embodiment the secondary balloon is external but adjacent to the sheath and prior to delivery the stent is disposed about the secondary balloon as well.

In some embodiments the rotating collar includes one or more inflation lumens for separate and/or simultaneous inflation of the primary and secondary balloons. To accommodate rotation without impairing balloon performance, in some embodiments the rotating collar comprises one or more sealing mechanisms which when in a sealed state prevents or limits rotation of the collar but which seals the collar to define one or more of the inflation lumens so that one or more of the balloons may be inflated. In at least one embodiment the sealing mechanism comprises one or more shape memory materials which may be moved between a free position and a sealed position upon exposure to a predetermined temperature, electrical signal, etc.(and/or for a predetermined period of time). In at least one embodiment the sealing mechanism is an inflatable seal which is in fluid communication with the secondary inflation lumen, such that when fluid is passed through the secondary inflation lumen to inflate the secondary balloon, the inflatable seal is expanded from a free state to a sealed state.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1 is a perspective view of an embodiment of the invention wherein the assembly is shown in a pre-deployment configuration.

FIGS. 2a-d are cross-sectional views of sheath configurations.

FIG. 3 is a perspective view of an embodiment of the invention wherein the assembly is shown having balloon cones on the balloon.

FIG. 4 is a perspective view of an embodiment of the invention wherein the assembly is shown having large diameter marking bands.

FIG. 11 is a side view of an embodiment of the invention, comprising a rotating sheath assembly.

FIG. 12 is a side view of the embodiment shown in FIG. 11 shown configured for delivery of a stent.

Figure 16:
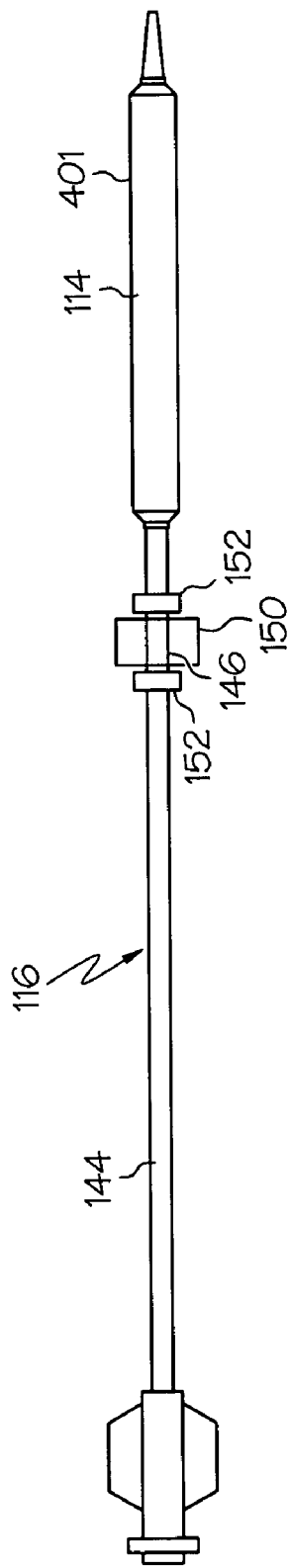
FIG. 16 is a side view of an embodiment of the invention comprising a catheter assembly. The catheter assembly is provided with a rotating collar.
Figure 17:
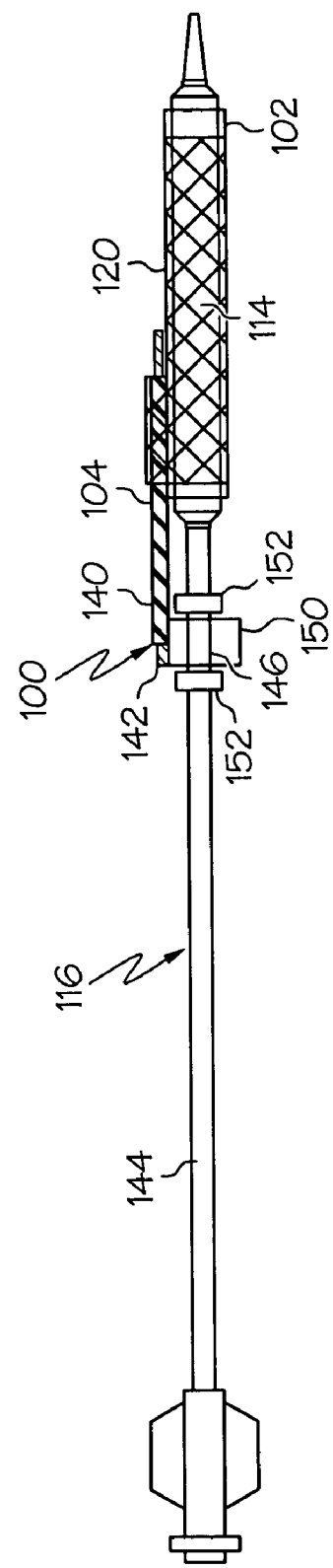
FIG. 17 is a side view of the catheter assembly of FIG. 16 and further comprising the rotating sheath assembly and stent of FIG. 12.
Figure 19:
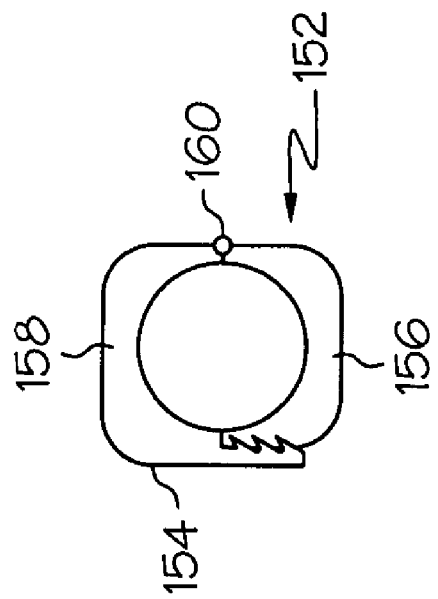
Figure 18:
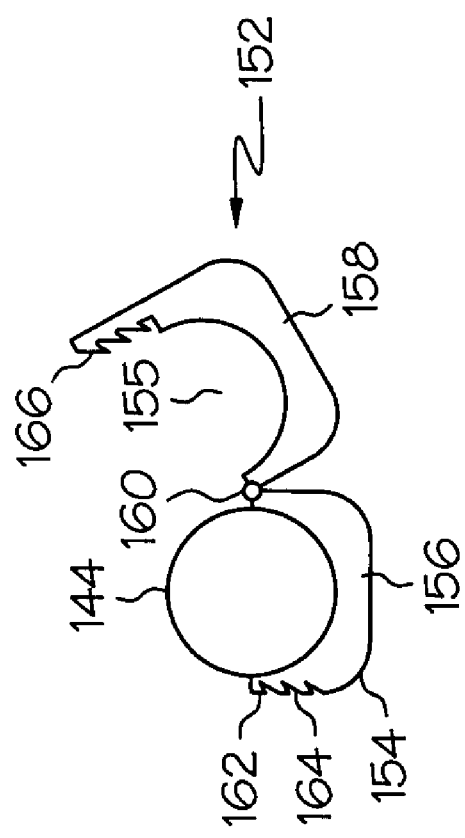

FIGS. 18-19 are cross-sectional views of an embodiment of the invention comprising a locking clip for use on a catheter such as is shown in FIGS. 16 and 17, wherein the clip, when mounted on the catheter shaft adjacent to the rotating collar, prevents longitudinal displacement of the collar and the associated rotating sheath assembly. In FIG. 18 the clip is shown in an open, unlocked configuration for placement and removal from a catheter shaft. In FIG. 19 the clip is shown in the closed, locked configuration such as the clip would have when positioned on the catheter shaft.

FIG. 20 is a partial side view of an embodiment of the invention wherein the catheter assembly includes a pair of cone retaining sleeves for aiding in retaining the folded configuration of the balloon prior to balloon expansion.

Figure 21:
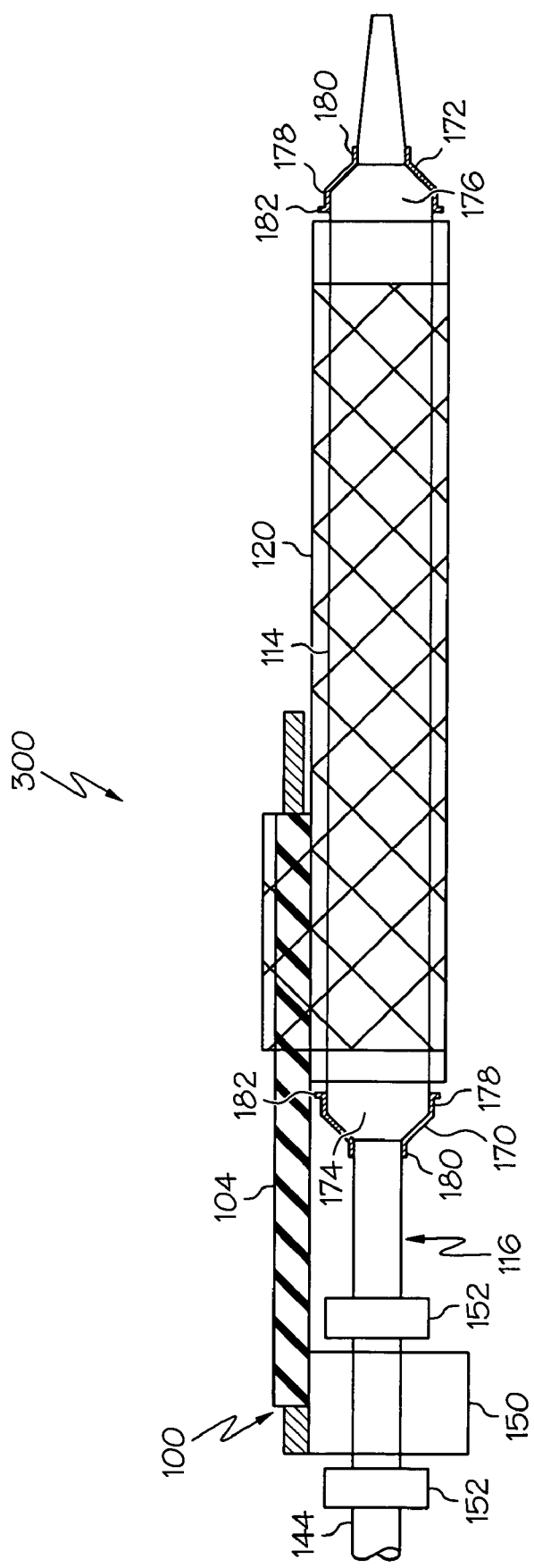

FIG. 21 is a partial side view of an embodiment of the invention similar to that shown in FIG. 20, but wherein each cone retaining sleeves further include radial ridges for preventing longitudinal displacement of the sleeve.

Figure 22:
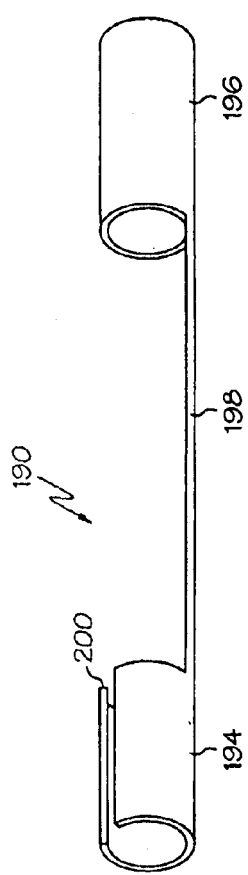

FIG. 22 is a perspective view of an embodiment of the invention comprising a removable protective sheath for retaining the balloon in the reduced or pre-delivery state.

Figure 23:
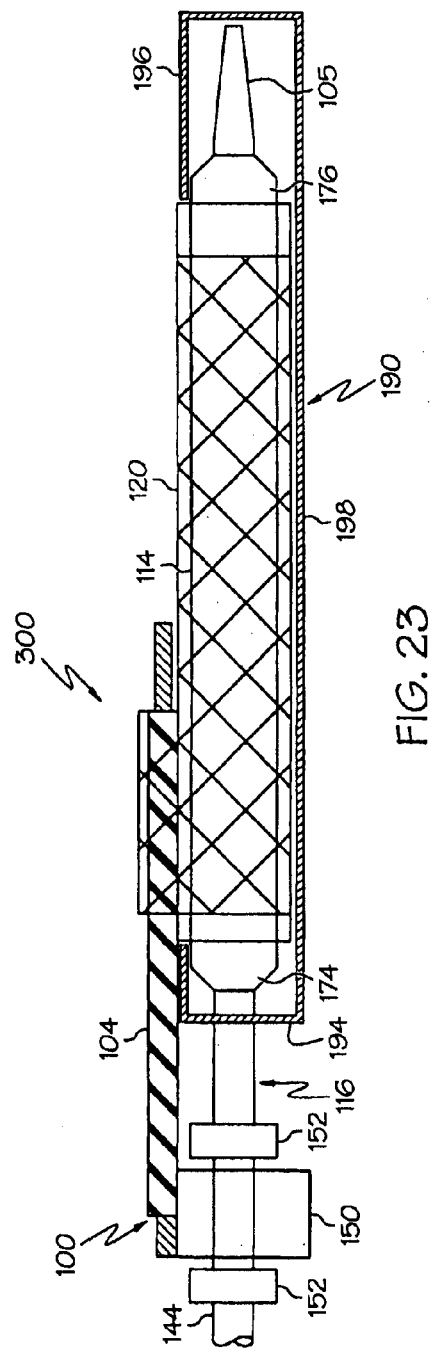

FIG. 23 is a side view of an embodiment of the invention wherein the catheter assembly is depicted with the protective sheath shown in FIG. 22 in place prior to use of the catheter.

Figure 24:
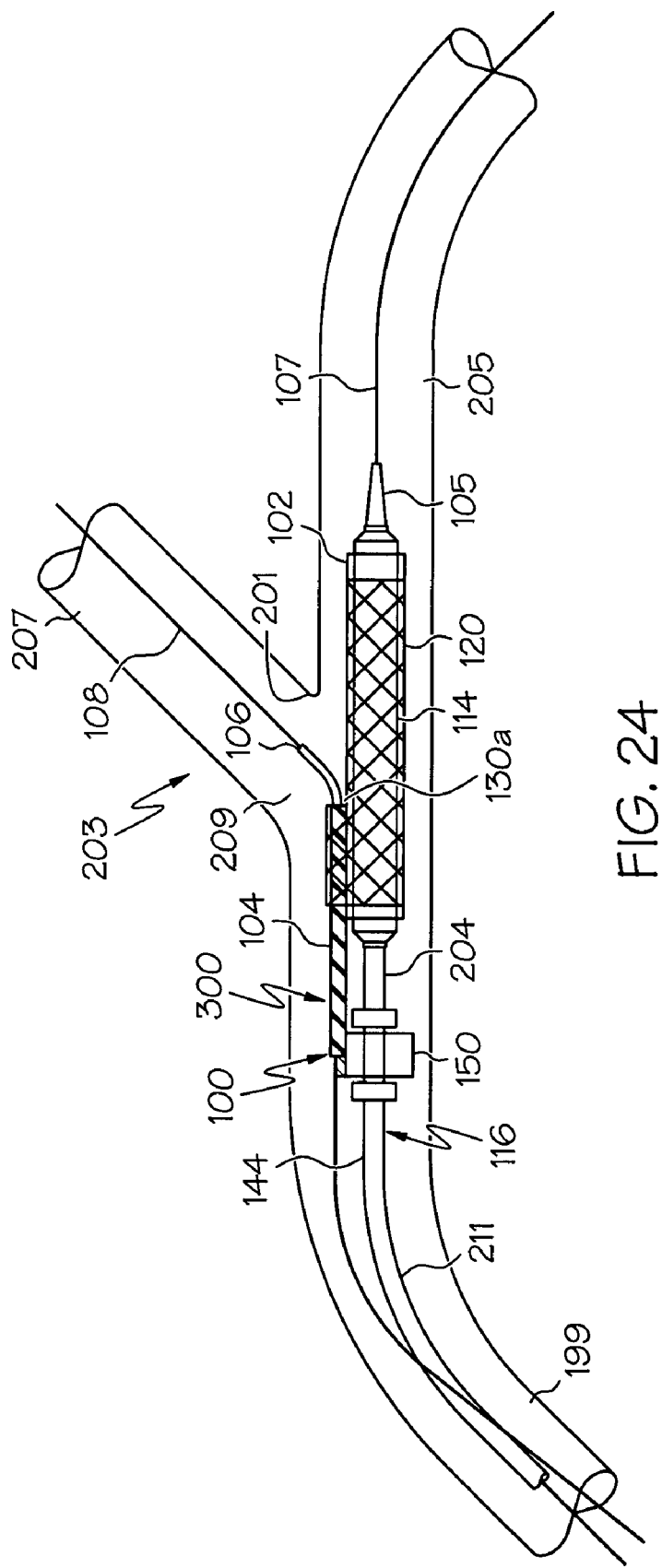

FIG. 24 is a side view of an embodiment of the invention wherein the catheter assembly of FIG. 17 is shown being advanced along a primary and secondary guide wire to a vessel bifurcation prior to delivery of the stent.

Figure 25:
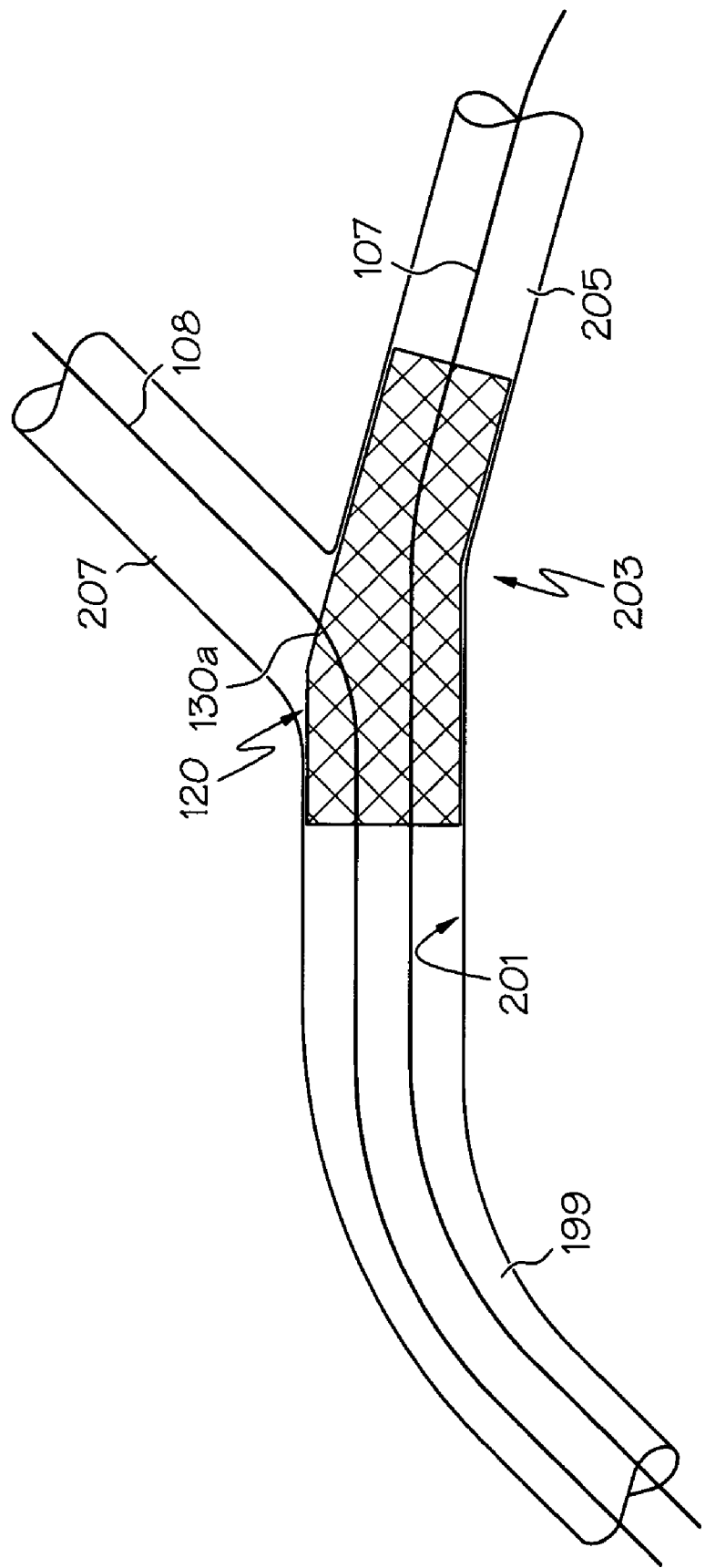

FIG. 25 is a side view of the stent depicted in FIG. 24, wherein the stent has been delivered from the catheter assembly, by balloon expansion and the assembly subsequently withdrawn from the vessel(s).

Figure 26:
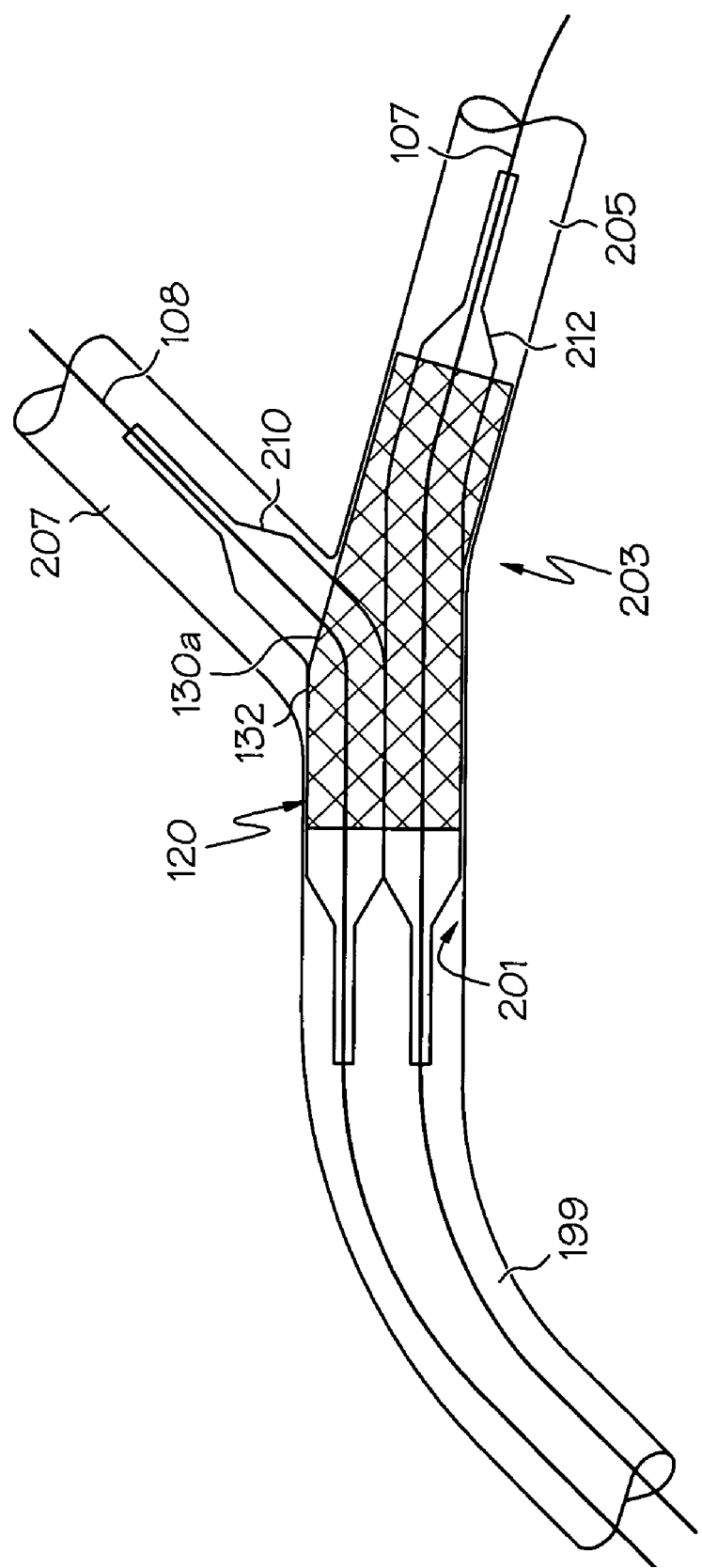

FIG. 26 is a side view of the stent of FIG. 25, depicted being seated within the vessel bifurcation by a pair of balloons, which are advanced individually along each guide wire and expanded within the stent and subsequently removed therefrom.

Figure 27:
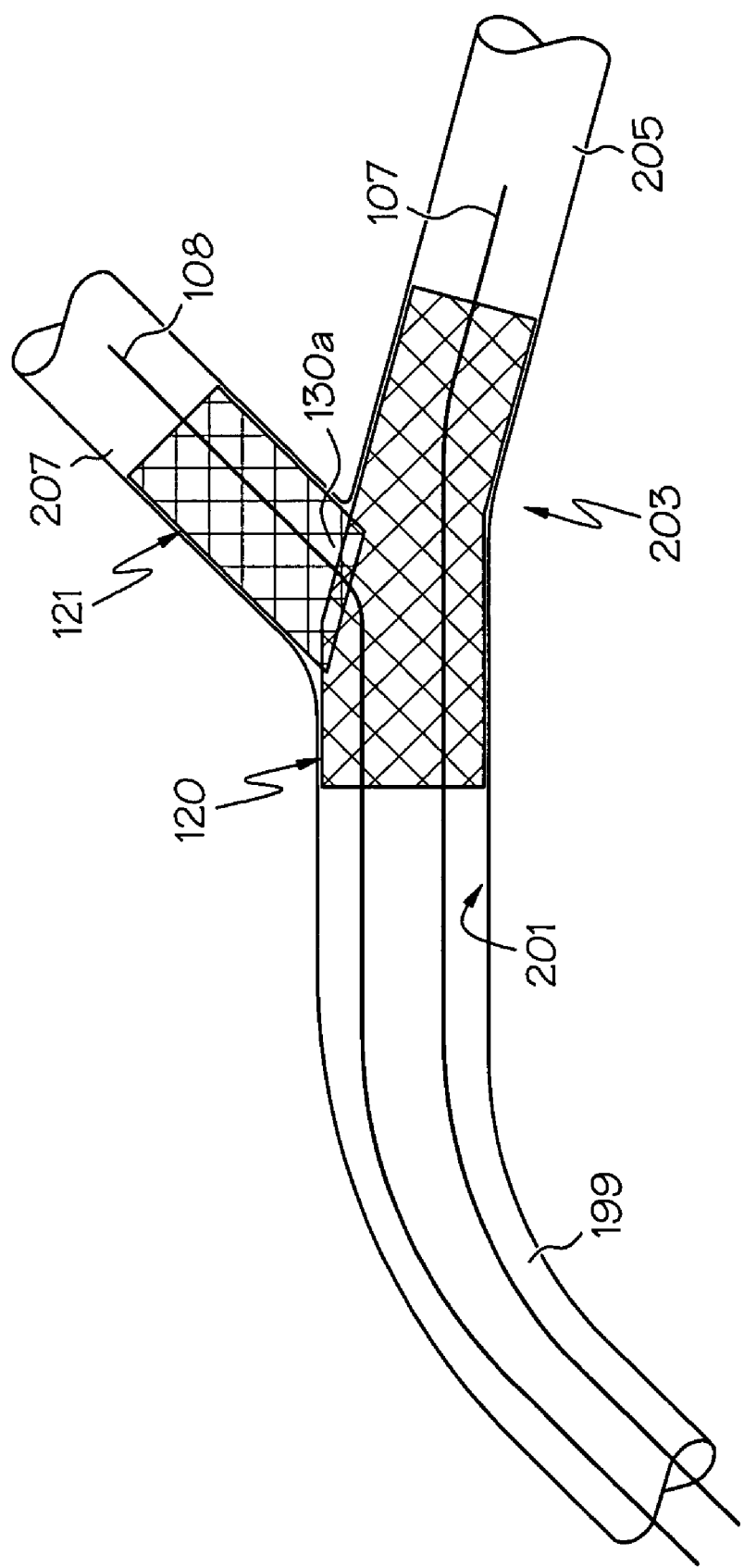

FIG. 27 is a side view of the stent shown in FIG. 26, (now referred to as the primary stent) wherein a secondary stent has been deployed by a stent delivery catheter through the secondary opening of the primary stent.

Figure 28:
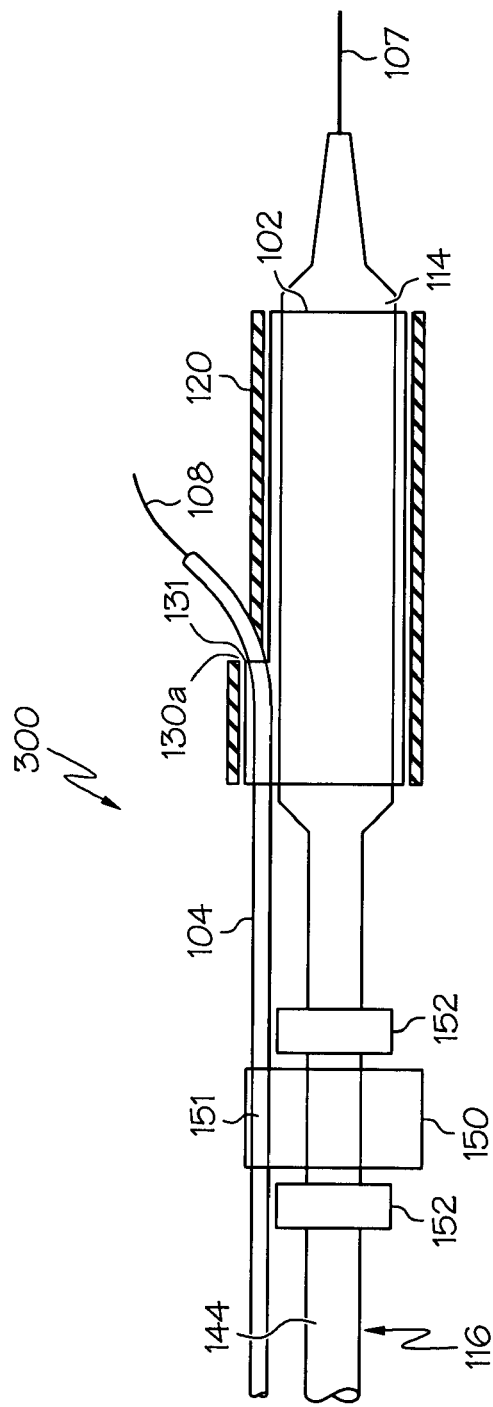

FIG. 28 is a side view of an embodiment of the invention comprising a catheter assembly wherein the secondary guide wire lumen extends from the rotating collar, under the rotating sheath and out a secondary openings of the sheath and stent.

Figure 29:
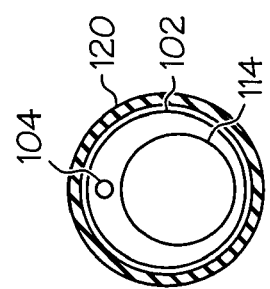

FIG. 29 is a cross-sectional view of the assembly shown in FIG. 28.

Figure 30:
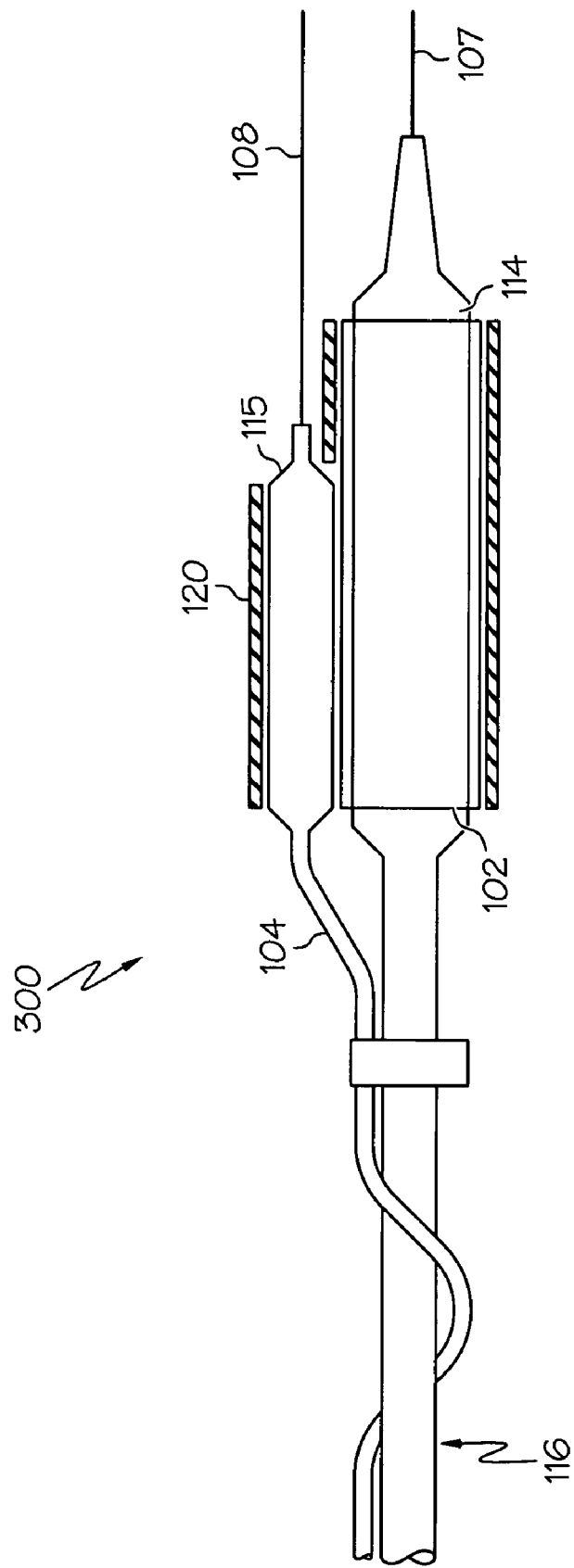

FIG. 30 is a side view of an embodiment of the invention comprising a catheter assembly having dual balloons wherein the secondary balloon is positioned radially adjacent the rotating sheath, but substantially within a portion of the stent, the secondary balloon is thus rotatable about the primary balloon by the rotation of the sheath.

Figure 31:
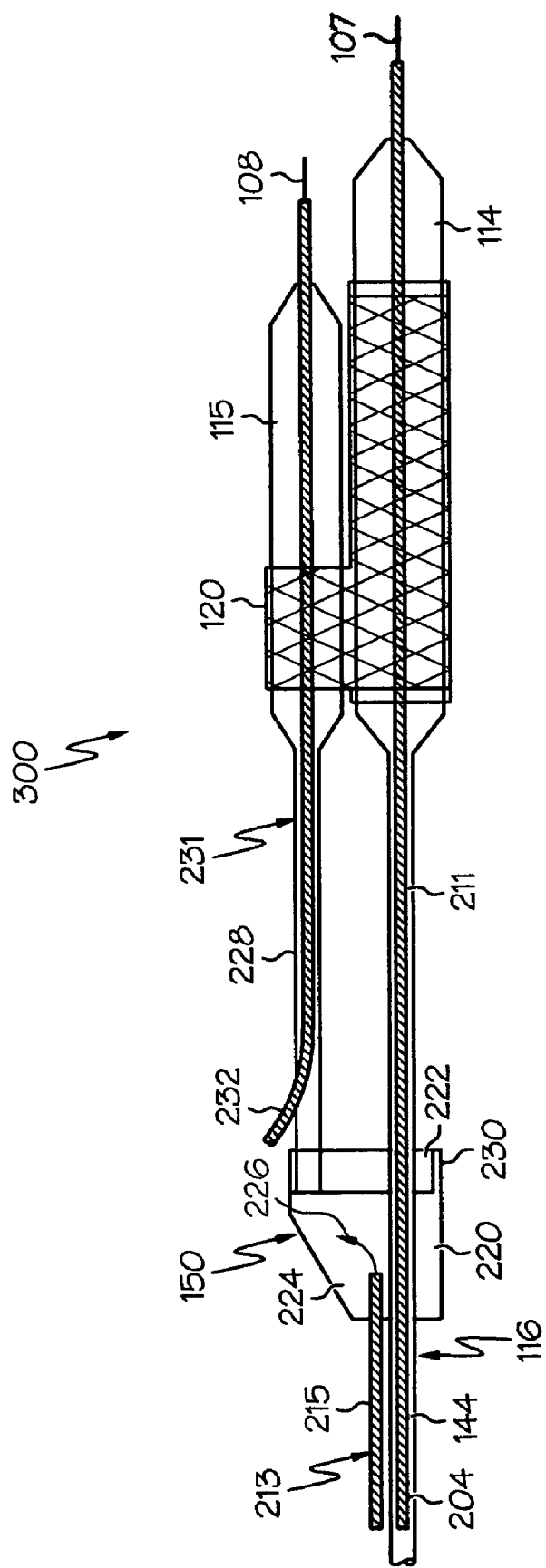

FIG. 31 is a perspective view of a catheter assembly having two inflation balloons, wherein the secondary balloon is in fluid communication with a secondary inflation lumen and the rotating collar provides a rotatable seal which allows the proximal portion of the secondary inflation lumen fluid communication with the distal portion of the secondary inflation lumen.

Figure 32:
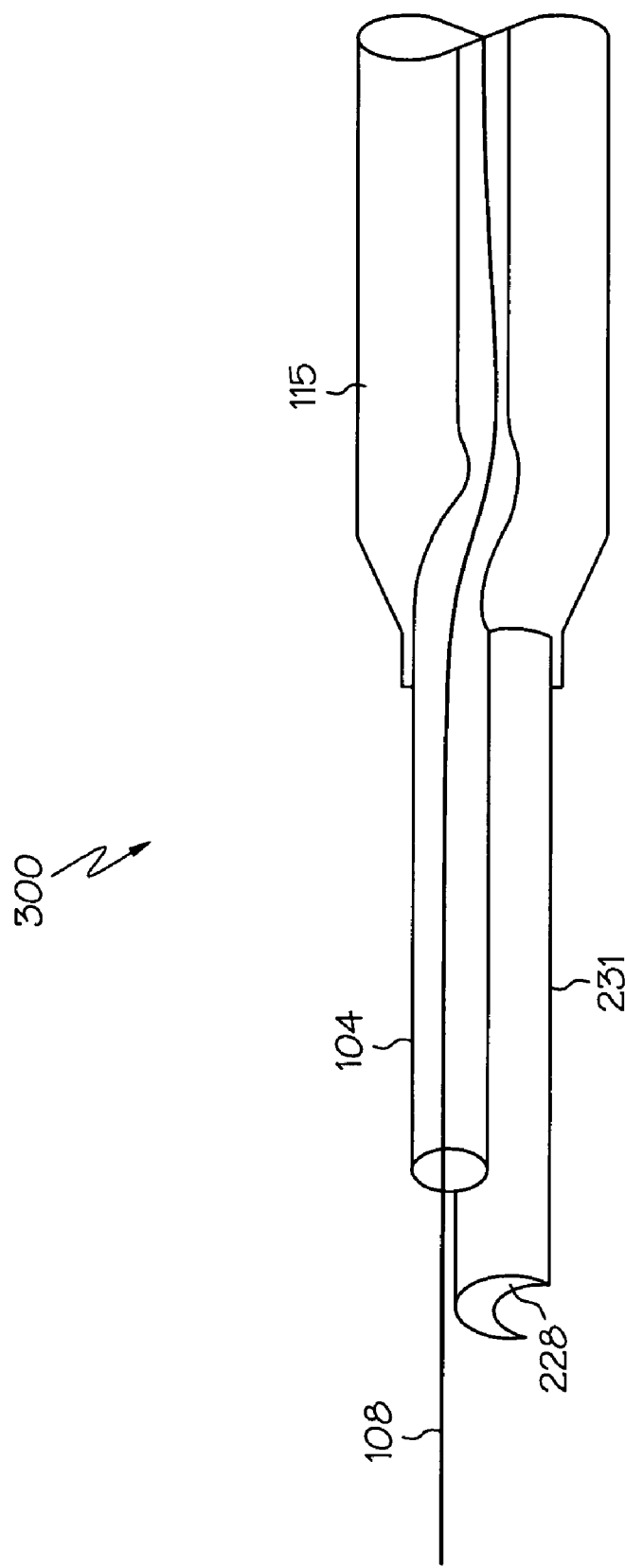

FIG. 32 is a perspective view of a portion of the assembly shown in FIG. 31, wherein the secondary inflation lumen is provided with a substantially crescent shaped cross-sectional shape to provide the secondary inflation lumen with a lower profile and improved rotational interface with the catheter shaft or primary inflation lumen.

Figure 34:
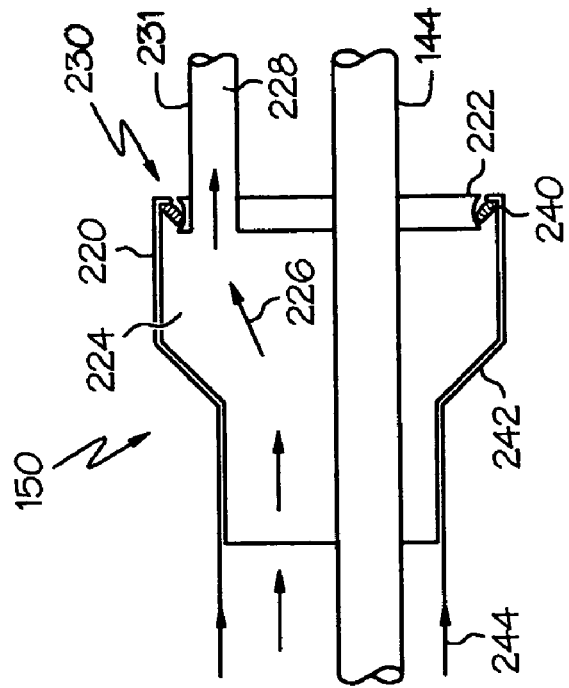
Figure 33:
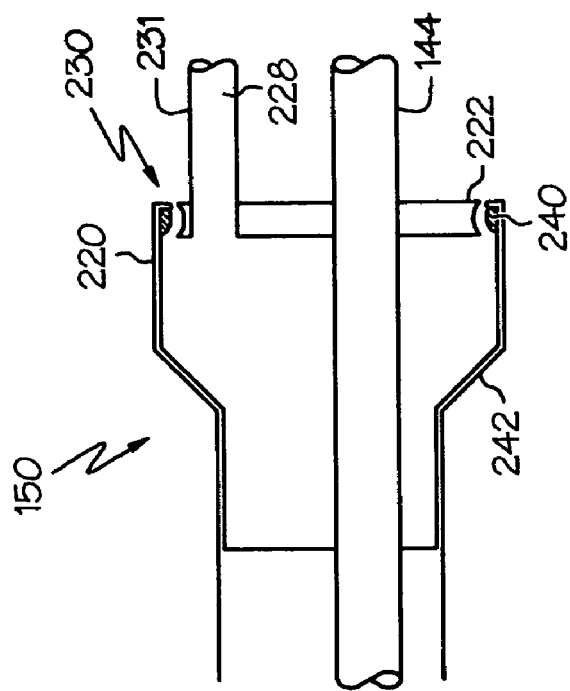

FIGS. 33-34 are side views of a configuration of rotating seal, shown in the open rotatable position and sealed fixed position respectively, for use in a catheter assembly such as is depicted in FIG. 31.

Figure 36:
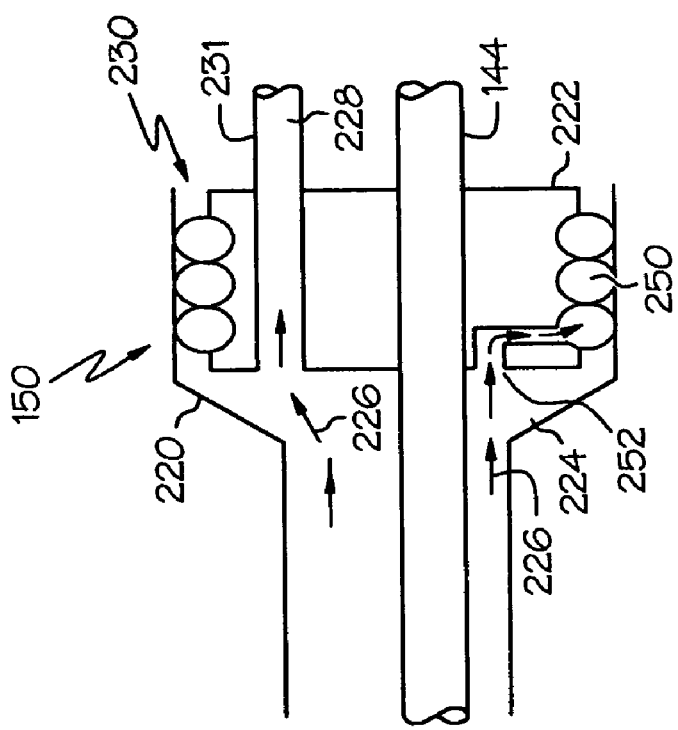
Figure 35:
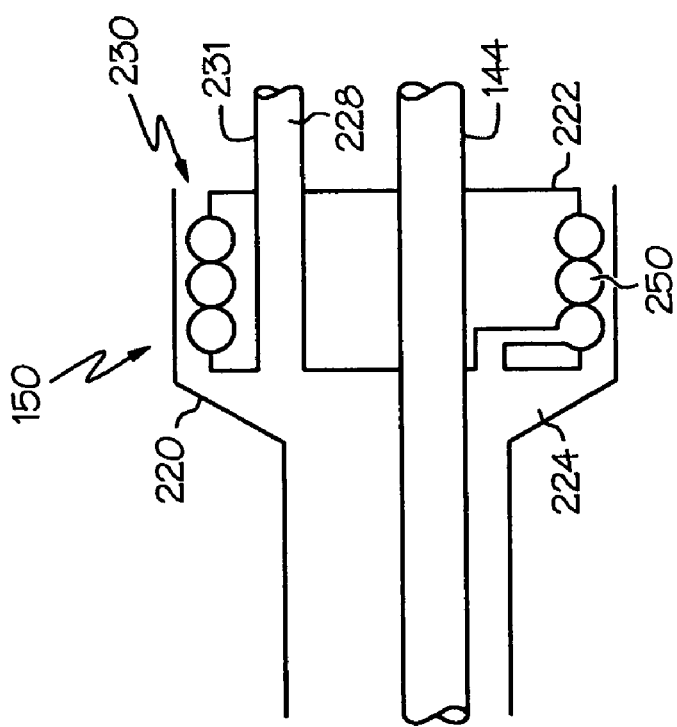

FIG. 35-36 are side views of a configuration of rotating seal, shown in the open rotatable position and sealed fixed position respectively, for use in a catheter assembly such as is depicted in FIG. 31.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, in at least one embodiment of the invention, an example of which is shown in FIG. 1, an assembly 10 is shown. The assembly is designed to provide better axial and longitudinal positioning of a stent in a bifurcation site. The assembly 10 has an outer catheter shaft 14 with an inner catheter shaft 16 defining a wire lumen 17 and an inflation lumen 18 extending from a proximal region of the catheter to a distal region of the catheter. The inner lumen 17 is constructed such that it can be disposed about a guide wire which provides means for guiding the catheter to the treatment site. The inflation lumen 18 provides a passage for the inflating fluid to both inflate and deflate the catheter balloon 20. The catheter balloon 20 is sealingly engaged at its proximal end 20a to the outer shaft 14 and is sealingly engaged at its distal end 20b to the inner shaft 16.

A sheath 22 is disposed about the balloon 20. The sheath is designed to be freely rotatable about the balloon. The sheath 22 can be constructed of a low friction material such as PTFE or HDPE which allows the sheath to freely rotate about the balloon 20. In some embodiments at least a portion of balloon 20 may include a coating of one or more low friction materials or include one or more low friction materials in its construction. In some embodiments the assembly 10 may be used to deliver a stent 24 to a vessel bifurcation. In such embodiments a stent 24 is disposed about and crimped upon the sheath 22. The rotatability of the sheath 22 allows a stent 24 disposed thereabout to be freely rotated within a vessel or lumen to allow one or more openings of the stent to be aligned with a branch of the bifurcation.

It should be noted that the sheath can also have multiple layers. An outer layer 22a of the sheath 22 may be constructed of a softer material than that of the material used in constructing the inner layer 22b of the sheath 22. The softer outer layer will provide improved stent securement upon crimping of the stent 24. In one embodiment, a soft polymer is one with a durometer hardness of less than about 55D. Possible materials for the outer layer are a polymer like PEBAX (55D), a urethane, etc. The low friction inner layer 22b can be constructed of PTFE or HDPE.

Figure 5:
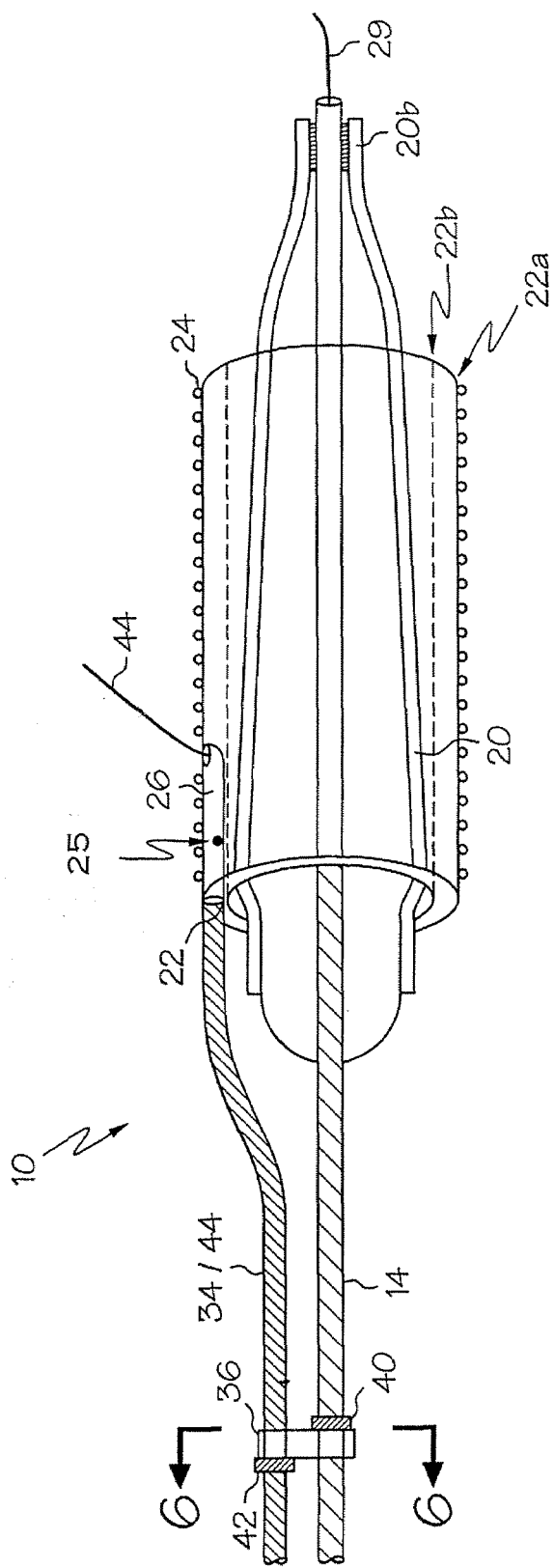
FIG. 5 is a perspective view of an embodiment of the invention wherein the assembly is shown illustrating the tether attachment and also the rotating collar and longitudinal locks.

A second shaft 25 defining the second wire lumen 26 is engaged along a portion of the sheath 22. The sheath itself can also define the second wire lumen 26. Rotational torque indicated by arrows 27 may be applied to the sheath 22 when the catheter is advanced to the bifurcation site in the following manner:

In some embodiments of the assembly 10 is advanced along two guide wires 29 and 44 as shown in FIG. 5. The first guide wire 29 is positioned in the primary passage or branch vessel and is disposed inside the inner lumen 17 of the catheter shaft 14. The second guide wire 44 diverges from the first guide wire 29 upon passage into the secondary branch in the region of the bifurcation. The inner lumen 17 of the stent delivery assembly 10 is disposed about the guide wire 29 in the primary passage while the second wire lumen 26 of the stent delivery assembly 10 is disposed about the second guide wire which extends into the secondary passage of the bifurcation. As the stent delivery assembly 10 approaches the bifurcation, the sheath 22 which is engaged to the second wire lumen 26 will then rotate so as to be aligned with the side wall passage at the bifurcation. A tether 34 can also be added in order to limit the distal movement of the sheath 22 in relation to the inner shaft 16. The tether 34 can be attached directly to the sheath at tether engagement point 11.

Figure 7:
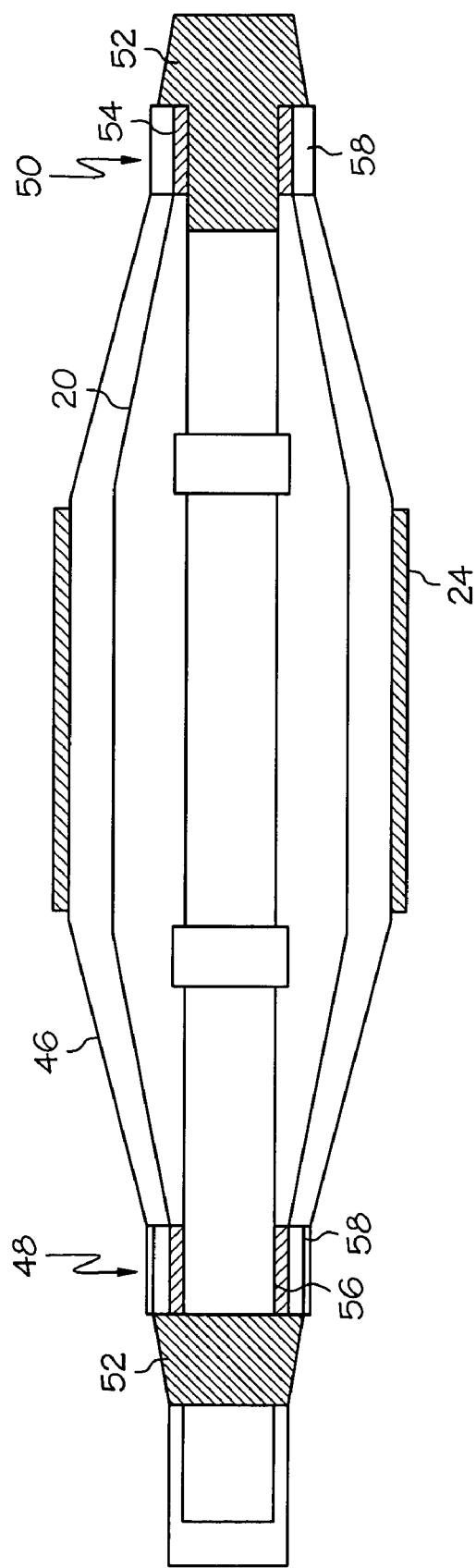
FIG. 7 is a perspective view of an embodiment of the invention wherein the assembly is shown having an outer balloon in place of the sheath.

The sheath or the outside balloon, as illustrated in FIG. 7, substantially freely rotates about the inner shaft 16 and/or balloon 20. The sheath or outside balloon may rotate less than a single degree or over 360 degrees in order to align at least one of the openings in the stent with a side branch lumen at a bifurcation site.

In FIGS. 2a-2c cross-sections of different embodiments of the shown sheath 22 in the unexpanded state prior to the delivery of the stent are illustrated. The second shaft 25 defining the second wire lumen 26 is engaged to the sheath 22. In another embodiment such as is shown in FIG. 2a a sheath having a second shaft 25a is attached to the sheath 22a. In a balloon expandable delivery system the sheath 22a is arranged in a coil-like structure before deployment of the stent. During delivery of the stent, the sheath 22a uncoils. In another embodiment such as is shown in FIG. 2b a sheath having a clam shell cross-section is shown in the unexpanded state. The second shaft 25b is engaged to the sheath at an end of the sheath 22b. In another embodiment such as is shown in FIG. 2c a sheath prior to delivery of the stent has a cross-section in the unexpanded state shaped in an accordion-like structure. The folds 28 in the unexpanded state can be pressed down or wrapped as shown in FIG. 2d.

In some cases it may be desirable to provide external protection of the sheath to prevent the sheath from being longitudinally displaced during advancement of the catheter and/or delivery of the stent. In FIG. 3 an embodiment is shown wherein the balloons end portions or cones 30 are provided with a diameter about the inner catheter shaft 16 greater than the cross-sectional diameter of the sheath 22. Thus, as a result of the position of the cones 30 about the ends of the sheath 22 the longitudinal movement of the sheath 22 relative to the inner catheter shaft 16 is limited. In another embodiment shown in FIG. 4, the sheath is protected by the inclusion of one or more hubs, protrusions, marker bands 32, etc. with a diameter sufficient to prevent the sheath from moving in a longitudinal direction. These marker bands 32 act like a dam on each end of the sheath 22 by forcing portions of the balloon radially outward such that these portions of the balloon 20 have a greater diameter than the diameter of the sheath 22. In the embodiments shown in FIGS. 3 and 4 the stent 24 in either or both the expanded and the unexpanded conditions may have a greater diameter than the cones 30 while the sheath 22 does not.

In FIG. 5 an embodiment of the invention is shown wherein the assembly is provided with a safety tether 34. The tether 34 (shown in this figure overlapping the second guide wire 44) can be a simple pull wire that runs along the length of the catheter 10 and engages the sheath 22. The tether 34 can extend into the second wire lumen 26 and thereby engage the sheath 22 or the second shaft 25 at an engagement point 35. The safety tether 34 can also attach to the sheath 22 directly as shown in FIG. 1 at tether engagement point 11.

Figure 6:
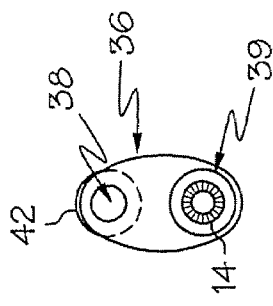
FIG. 6 is a cross-sectional view of the rotating collar from view A-A of FIG. 5.

As shown in the cut away portion of FIG. 5 and in FIG. 6 the catheter 10 may include a rotating collar 36 having a second guide wire collar lumen 38 and an outer catheter shaft collar lumen 39 which is disposed about the outer catheter shaft 14. A distal longitudinal lock 40 disposed about the catheter shaft and both adjacent and distal to the collar 36 limits longitudinal movement of the collar 36. The distal longitudinal lock 40 has a diameter greater than the diameter of the outer catheter shaft collar lumen 39. The proximal longitudinal lock 42 disposed about a second guide wire 44 has a greater diameter than the second guide wire collar lumen 38, thus limiting the wire 44 from distal movement beyond the point when the proximal longitudinal lock 42 comes into contact with the second guide wire collar lumen 36.

In FIG. 7 an outer balloon 46 which rotates around the inner balloon 20 is used in place of a sheath 22. In such embodiments the outer balloon 46 is sealed at first end 48 and second end 50 of the catheter 10. Balloon movement stoppers 52 limit longitudinal movement of the balloons. The outer balloon 46 can be constructed of a low friction material such as PTFE, HDPE and/or PEBAX which allows the outer balloon 46 to freely rotate about the inner balloon 20. The stent 24 is disposed about and crimped upon the outer balloon 46. It should be noted that the outer balloon can also have multiple layers. An outer layer of the outer balloon 46 may be constructed of a softer material than that of the material used in constructing the inner layer of the outer balloon 46. Where the balloon is provided with a softer outer layer, the softer outer layer may provide improved stent securement upon crimping of the stent 24. In one embodiment, a soft polymer is one with a durometer hardness of less than about 55D. Possible materials for the outer layer are a polymer like PEBAX (55D), a urethane, etc. The low friction inner layer of the outer balloon 46 can be constructed of PTFE or HDPE and/or other suitable materials.

In the embodiment shown in FIG. 7 the outer balloon 46 is rotatable about the inner balloon 20. Gap 58 (shown on only one end, first end 48) acts as a friction reducing mechanism between outer balloon seal site 54 and inner balloon seal site 56. Gap 58 includes a friction reducing fluid, a low friction material, a bearing system, etc., or any combination thereof.

Figure 8:
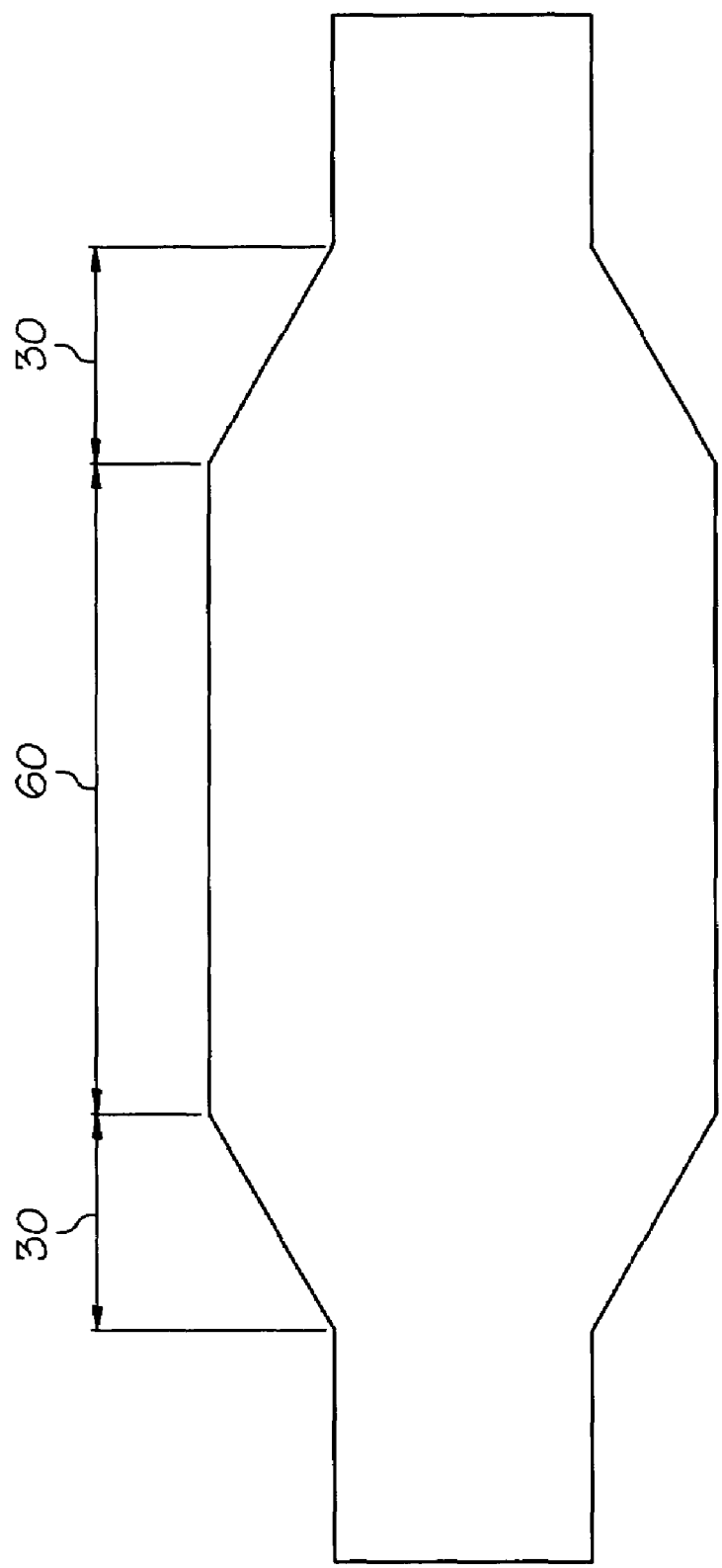
FIG. 8 is a perspective view of a catheter balloon illustrating the body portion and the cone portions of the catheter balloon.

In the embodiment shown in FIG. 8 the cones 30 and body portion 60 of the catheter balloon 20 are shown. In some embodiments of the invention the sheath 22 is of the substantially same length as the body portion 60 of the catheter balloon 20. In some embodiments the sheath 22 is disposed substantially on the body portion 60 of the balloon 20. In other embodiments the sheath 22 extends longitudinally such that a portion of the sheath 22 is disposed about at least one of the cone portions 30.

Figure 9:
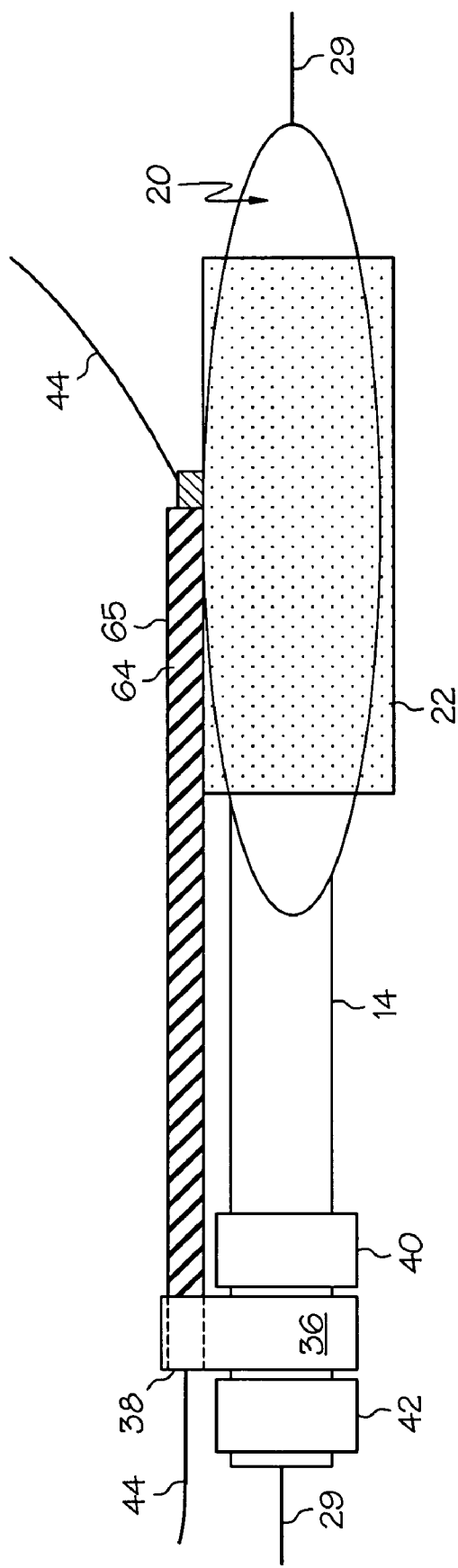
FIG. 9 is a perspective view of an embodiment of the invention wherein the assembly is shown having a hypotube which is disposed in the second guide wire collar lumen.
Figure 10:
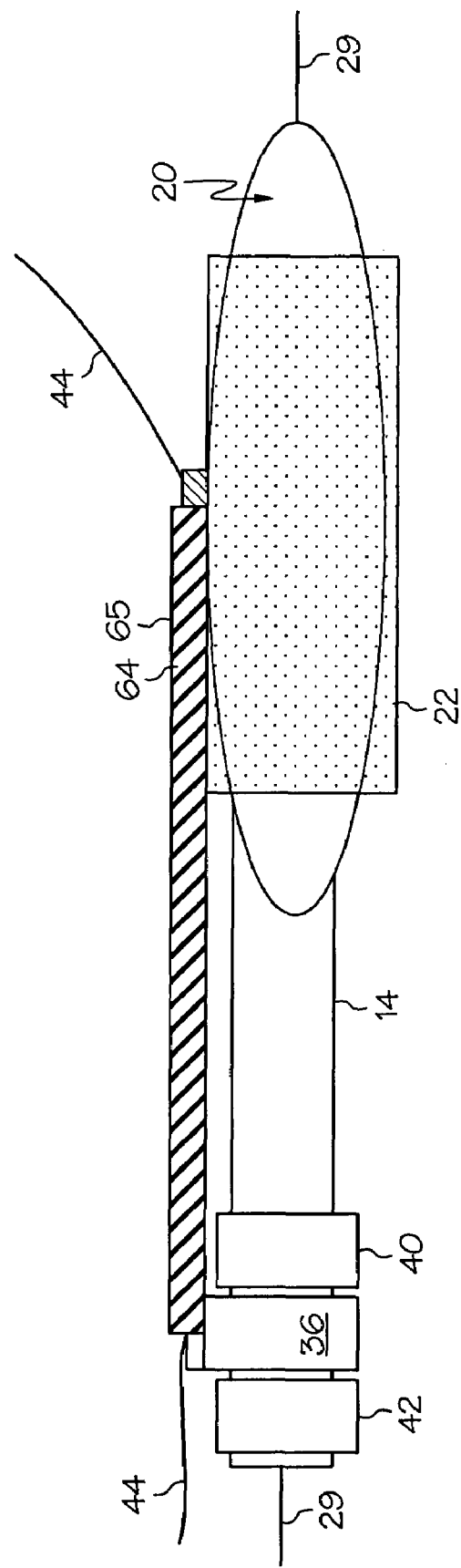
FIG. 10 is a perspective view of an embodiment of the invention wherein the assembly is shown having a hypotube engaged to the collar.

In the embodiments of FIGS. 9 and 10 a hypotube 64 is engaged to the collar 38 and the sheath 22. The hypotube 64 may comprise stainless steel or it may comprise a polymer. The hypotube 64 may be constructed to be spiral cut. The spiral cut 65 may include scoring, cutting, indenting, perforating, puncturing, etc. The hypotube 64 may thus be firm in the longitudinal direction but may also be flexible due to the spiral cut.

FIGS. 9 and 10 also illustrate embodiments having both the proximal longitudinal lock 42 and the distal longitudinal lock 40 disposed about the outer catheter shaft 14 rather than as shown in FIGS. 5 and 6 wherein one longitudinal lock is disposed about the guide wire 44 or safety tether 34.

FIG. 9 specifically illustrates an embodiment wherein the hypotube 64 is disposed in the second guide wire collar lumen 38. The hypotube 64 may be disposed in only a portion of the second guide wire collar lumen 38. The collar 36 rotates along with the sheath 22 and thus may rotate simultaneously and/or with equal degrees of rotation. In FIG. 10 the hypotube 64 is engaged to an outside surface of the collar 36. In both FIGS. 9 and 10 engagement of the hypotube 64 to the collar 36 and sheath 22 can be through chemical welding, heat welding, laser welding, chemical bonding, adhesives, fastening devices, etc.

Turning now to the embodiment shown in FIG. 11 a rotating sheath assembly 100 is shown which comprises a tubular sleeve or sheath 102 and a positioning or secondary guide wire housing 104, the housing 104 defines a secondary guide wire lumen 106 through which a secondary guide wire 108 may be passed.

Though the housing 104 may be constructed of a wide variety of materials including metal plastic, etc., in at least one embodiment the housing 104 is a hypotube 64 as has been previously described. In some embodiments the housing 104 is provided with one or more openings 110 along its length. In at least one embodiment the housing 104 is spiral cut to provide at least a continuous opening 110 which acts to provide improve the flexibility of the housing 104.

In at least one embodiment the secondary guide wire housing 104 further comprises an inner shaft 103, about which the hypotube 64 is disposed. In at least one embodiment the inner shaft 103 is a flexible hollow tubular member which extends distally beyond the distal end of the hypotube 64. This distal tip 105 of the inner shaft 103 provides the housing with a flexible protective sheath about the guide wire 108 as it passes distally out of the secondary guide wire lumen 106. Such a protective covering prevents the guide wire 108 from excessively rubbing against the wall 201 of the vessel 199, such as in the manner depicted in FIG. 24, even where the secondary guide wire 108 exits the secondary lumen 106 at a significant angle. The inner shaft 103 may be constructed of any of a variety of flexible materials such as: PEBAX, nylon, urethane, and/or other materials in a single layer, multi-layer and/or braided configuration.

In some embodiments at least a distal portion of the housing 104 is engaged to at least a proximal portion of the sheath 102 at an engagement site 112. The manner or mechanism of engagement between the sheath and housing 104 may be by bonding, welding, adhering adhesively engaging, mechanically engaging or otherwise connecting the surfaces of the respective sheath 102 and housing 104.

The sheath 102 is a hollow tube of sheath material that is configured to be placed over the balloon 114 of a catheter assembly 116, such as in the manner illustrated in FIGS. 16 and 17. The sheath 102 is further configured to be rotatable about the balloon 114, even when a stent 120 has been positioned about and/or affixed to the sheath 102.

In order to ensure that the sheath 102 is rotatable about a balloon 114, even with a stent 120 crimped on to the sheath 102 and the catheter is being advanced through the a body, the sheath 102 may be constructed of a variety of low friction materials such as PTFE, HDPE, etc. In at least one embodiment the sheath 102 is at least partially constructed of a hydrophilic material, such as hydrophilic polymers such as; TECOPHLIC® material available from Thermedics Polymer Products, a division of VIASYS Healthcare of Wilmington, Mass.; TECOTHANE®, also available from Thermedics Polymer Products; hydrophilic polyurethanes, and/or aliphatic, polyether-based thermoplastic hydrophilic polyurethane; and any other material that provides the sheath 102 with the ability to rotate freely about the balloon 114 when in the "wet" state, such as when the catheter is exposed to body fluids during advancement through a vessel. Suitable sheath materials may also provide the sheath with rotatability in the "dry", or pre-insertion, state, but with the application of a greater amount of force than when in the wet state, such materials are referred to herein as being TECOPHLIC®.

A sheath 102 at least partially constructed from TECOPHLIC® material provides the sheath 102 with the ability to rotate freely about the balloon 114 when in the "wet" state, such as when the catheter is exposed to body fluids during advancement through a vessel. The TECOPHLI® C sheath 102 is also capable of rotation in the "dry", or pre-insertion, state, but with the application of a greater amount of force than when in the wet state.

A sheath 102 at least partially constructed from tecophilic material provides the sheath 102 with the ability to rotate freely about the balloon 114 when in the "wet" state, such as when the catheter is exposed to body fluids during advancement through a vessel. The tecophilic sheath 102 is also capable of rotation in the "dry", or pre-insertion, state, but with the application of a greater amount of force than when in the wet state.

In some embodiments the sheath 102 may be constructed of one or multiple materials, in one or more layers. For example, the sheath 102 may comprise an outer layer of a softer material than that of the material used in constructing an inner layer, such as has been previously described. In some embodiments, an example of which is shown in FIG. 11, the sheath 102 may be comprised of a matrix of a first material 111 and have one or more supportive stripes, strands, members or areas of a second supportive material 113 within, external to or internal to such a matrix.

The composition of the sheath 102 material, whether a single, multiple layer or stripe reinforced extrusion may include essentially any appropriate polymer or other suitable materials. Some example of suitable polymers include Hydrophilic Polyurethanes, Aromatic Polyurethanes, Polycarbonate base Aliphatic Polyurethanes, Engineering polyurethane, Elastomeric polyamides, block polyamide/ethers, polyether block amide (PEBA, for example available under the trade name PEBAX), and Silicones, Polyether-ester (for example a polyether-ester elastomer such as Arnitel available from DSM Engineering Plastics), Polyester (for example a polyester elastomer such as Hytrel available from Du Pont), or linear low density polyethylene (for example Rexell).

Example of suitable re-inforcing materials whether alone or blended with other materials, mixtures or combination or copolymers include all Polyamides (for example, Durethan available from Bayer or Cristamid available from ELF Atochem), polyethylene (PE). Marlex high-density polyethylene, polyetheretherketone (PEEK), polyimide (PI), and polyetherimide (PEI), liquid crystal polymers (LCP), and Acetal (Delrin or Celcon).

In some embodiments the inner surface of the sheath 102 or the outer surface of the balloon 114 may include a coating of one or more low friction materials or include one or more low friction materials in its construction. Such a coating 401 is shown in FIG. 16, as being depicted on the surface of the balloon 114 before assembly 100 has been placed thereabout, such as is depicted in FIG. 17. Coating 401 may however by placed between the balloon 114 and sheath 102 at any time. Some examples of a suitable coating material include but are not limited to: hydrogel, silicon, and/or BIOSLIDE® .available from SciMed Life Systems, Inc. of Maple Grove Minn.

As mentioned above, the sheath 102 is configured to be freely rotatable about a balloon of a catheter even when a stent 120, such as is shown in FIG. 12 is crimped onto the sheath 102. When properly positioned on the sheath 102, a proximal portion 122 of the stent 120 is also disposed about at least a portion of the secondary guide wire housing 104. When properly positioned about the sheath 102 and the housing 104, at least a portion of the housing 104 and/or the secondary guide wire 108 extends distally through a cell opening 130 of the stent 120.

Figure 13:
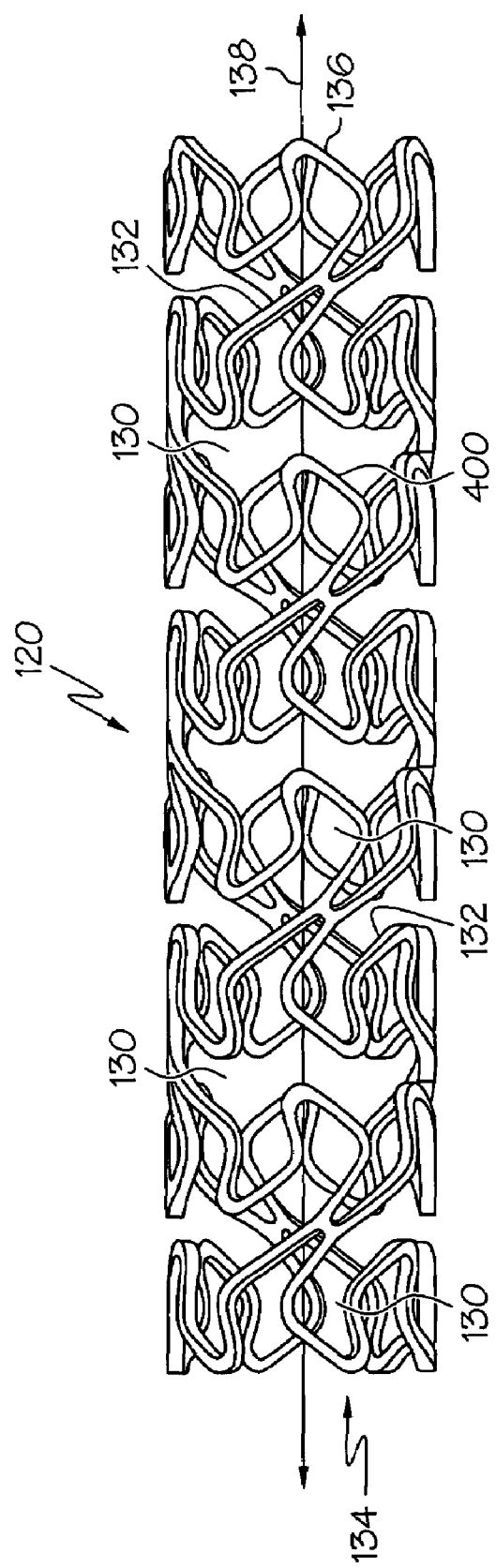
FIG. 13 is a side perspective view of an embodiment of the invention comprising a stent, such as that shown in FIG. 12.

Stent 120 may be a stent, such as is shown in FIG. 13, which is at least partially constructed of a plurality of interconnected struts, connectors or members 132. The stent 132 defines a proximal opening 134, a distal opening 136 and a flow path 138 therebetween. The cell openings 130 are in fluid communication with the flow path 138.

When the secondary guide wire 108 and/or the secondary guide wire housing 104 is threaded through one of the cell openings 130 when the stent is positioned onto the assembly 100, such as is shown in FIG. 12, the members 132 that define the selected cell opening 130a, as well as the shape of the opening 130a through which the secondary guide wire 108 exits the stent, may be distorted or modified in order to accommodate the passage of secondary guide wire 108 and/or the secondary guide wire housing 104 therethrough.

Figure 14:
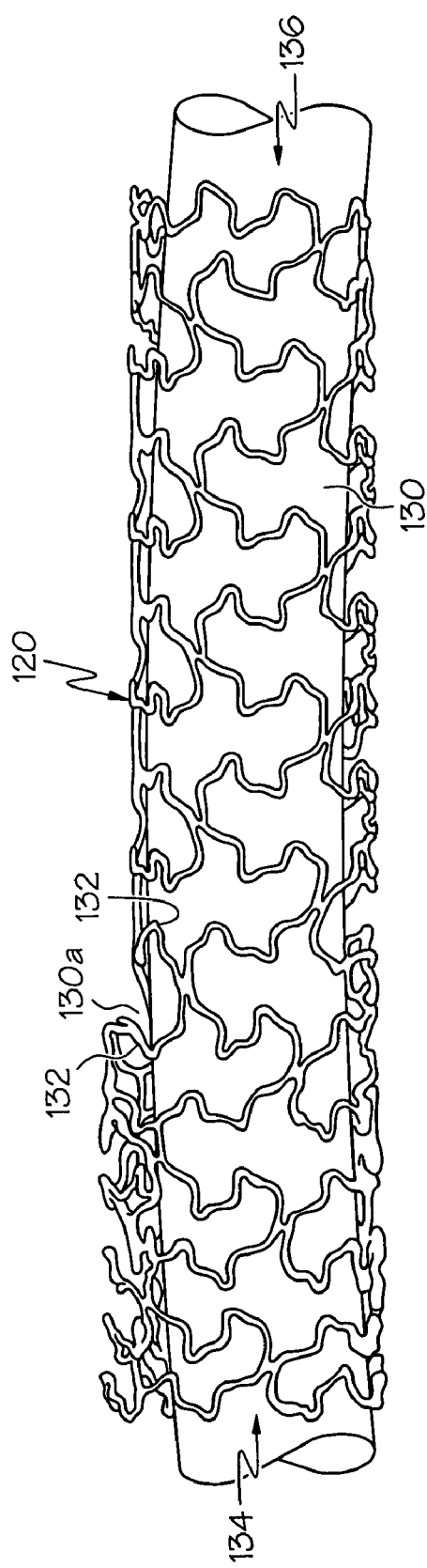
FIG. 14 is a side perspective view of the stent shown in FIG. 13 wherein a side branch opening is shown formed from the enlargement of a cell opening in the stent wall.
Figure 15:
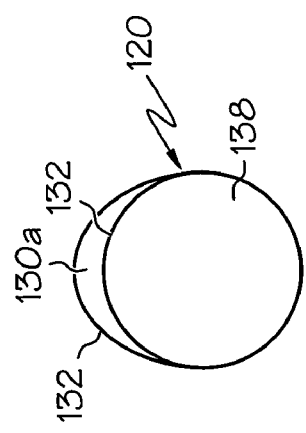
FIG. 15 is a cross-sectional view of the stent of FIG. 14.

The modified cell opening 130a, hereinafter referred to as secondary opening 130a, is positioned on the stent 120 between the proximal opening 134 and the distal opening 136. The manner in which the secondary opening 130a, the members 132 adjacent thereto, and to an extent the stent 120 itself, are modified or distorted by the position of the secondary guide wire and/or secondary guide wire housing is depicted in FIGS. 14 and 15.

It should be noted that when the stent 120 is placed on the assembly in the manner described above, the distortion of the secondary opening 130a and the adjacent members 132 is of a minimal extent, and is provide only to allow sliding passage of the secondary guide wire 108, and if desired a distal portion of the secondary guide wire housing 104, through the secondary opening 130a. As such, the actual size of the secondary opening 130a may be substantially similar, or only marginally different than that of the surrounding cell openings 130.

It should also be further noted that while stent 120 may be a standard "single vessel" stent that is provided with a secondary opening 130a in the manner described above, the stent 120 may also be a bifurcated stent having a trunk or stem portion, with one or more leg portions and/or branch openings adjacent thereto, through one of which the secondary guide wire may be passed. Such bifurcated stents and stent assemblies are well known in the art.

In at least one embodiment the stent 120, or one or more portions thereof, may be configured to deliver one or more therapeutic agents to a delivery site such as within the vessel 199 or one or more areas adjacent thereto, such as shown in FIGS. 24-27. In some embodiments one or stent members 132, such as is shown in FIG. 13, maybe configured to include one or more holes, notches, or other surface features to which one or more therapeutic agents 400 may be placed for delivery to the aneurysm site. A therapeutic agent may be placed on the stent in the form of a coating. In at least one embodiment the coating includes at least one therapeutic agent and at least one polymer.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vasco-active mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are $Lin^-$, $Sca-1^+$, $c-Kit^+$, $CD43^+$, $CD45^+$, $CD34^-$ $Lin^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

$Lin^-CD34^-$—Although $CD34^+$ cells have received much attention, many articles have been published lately which suggest the most primitive bone marrow derived stem cells are $CD34^-$ $Lin^-CD34^+$—Presence of the cell surface protein CD34 has been used to identify hematopoietic stem cells. However, the marker is also present on progenitor cells and white blood cells of various levels of maturity.

$Lin^-cKit^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the 6$^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In at least one embodiment an example of a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

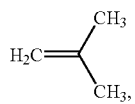

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

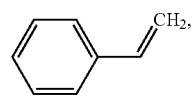

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

Once the stent 120 is positioned on the assembly 100, such as in the manner shown in FIG. 12, the assembly 100 may be slid onto a catheter 116, such as is shown in FIGS. 16-17 so that the sheath 102 is rotatingly disposed about the balloon 114 and a proximal portion 140 of the secondary guide wire housing 104 is engaged to a rotating collar 150.

The collar 150 is engaged to the proximal portion 140 of the secondary guide wire housing 104 by any engagement mechanism desired, such as welding, bonding, mechanical engagement, adhesive engagement, etc. In the embodiments shown in FIG. 17 for example, the proximal portion 140 of the secondary guide wire housing 104 and the collar 150 are engaged externally at engagement site 142. In some embodiments the secondary guide wire housing 104 may be passed at least partially through the collar 150, and/or the collar 150 may define a lumen through which the secondary guide wire 108 may be passed before entering into the secondary guide wire housing 104.

Collar 150 may be a substantially cylindrical member that is disposed about the shaft 144 of the catheter 116 at a position proximal of the balloon 114. The collar 150 may be characterized as defining a catheter shaft lumen 146 through which the catheter shaft 144 is passed. In order to provide the collar 150 with the ability to freely rotate about the catheter shaft 144, the collar 150 defines a catheter shaft lumen 146 which has a diameter greater than the outer diameter of the shaft 144. In some embodiments one or more lubricious substances may be placed between the collar 150 and the shaft 144 to further encourage free rotation therebetween.

While the rotating collar 150 is free to rotate about the shaft 144, in some embodiments it will also be capable of being longitudinally displaced along the shaft 144 as well. As such, in some embodiments one or more locks or hubs 152 may be affixed about the shaft 144 on one or both sides of the collar 150 to prevent or limit the potential longitudinal displacement of the collar 150 relative to the shaft 144.

In at least one embodiment, shown in FIGS. 18-19, a lock 152 comprises a body 154 which defines a catheter shaft engagement area 155. The body 154 is divided into at least two sections 156 and 158 which are pivotally moveable between an open position, shown in FIG. 18, and a closed or secured position (about the catheter shaft 144), shown in FIG. 19. The sections 156 and 158 are pivotally engaged to one another by apivot 160. The body 154 may be two completely separatable sections 156 and 158, may be a single member with sections 156 and 158 flexibly and pivotally engaged to one another, etc.

In the open position, shown in FIG. 18, the shaft 144 is positioned in the catheter shaft engagement area 155, the sections 156 and 158 are secured together to fixedly engage the lock 152 about the shaft 144. In at least one embodiment, section 156 defines a receiving chamber 162 having a grasping mechanism 164 for retainingly engaging a locking tab 166 of the adjacent section 158. The chamber 162 and/or tabl66 may comprise any ofa plurality of engagement mechanisms to fixedly engage the section to one another. For example, they may employ one or more complimentary surface features which securingly engage the adjacent surfaces of the chamber 162 and tab 166.

It is noted that a lock 152 may have any external shape desired and is preferably shaped and sized to have a minimum of profile and shape so as to not interfere with the advancement and/or trackability of the catheter 116.

When secured about the catheter shaft 144, adjacent to the collar 150, a lock 152 will prevent the collar 150 from being longitudinally displaced along the catheter shaft 144 in the direction of the lock 152. Where two locks 152 surround the collar 150, the locks may be spaced so as to eliminate longitudinal displacement of the collar 150 or merely limit such displacement to a desired extent.

In practice, the assembly 100 may be affixed to a catheter 116 at any time prior to use in a stent delivery procedure. However, it is recognized that because the sheath 102 is free to rotate about the balloon 114 the sheath may not aid significantly in maintaining the balloon in a reduced, and typically folded, state prior to inflation of the balloon 114 and expansion of the stent 120. As a result, in some embodiments, particularly those wherein the balloon is to be retained in the reduced configuration for a lengthy time, it is desirable to provide a mechanism by which the balloon 114 is retained in the reduced state without interfering with the rotatability of the assembly 100 or otherwise compromising the intended level of performance of the system.

An example of a first type of such a balloon retaining mechanisms that aids in retaining the balloon in the reduced configuration but which does not interfere with the performance of the system both prior to and during the use of the catheter is shown in FIGS. 20 and 21, wherein the catheter 116 is depicted already equipped with the rotating assembly 100 and stent 120, and is further provided with a pair of balloon retaining sleeves 170 and 172. Prior to expansion of the balloon 114, a first portion 178 of each sleeve 170 and 172 is disposed about a respective proximal portion 174 or distal portion 176 of the balloon 114. Each of the proximal portion 174 and distal portion 176 of the balloon 114 may include at least a part of the balloon cone and in some embodiments at least a respective end portion of the balloon body adjacent thereto. The second portion 180 of each sleeve is engaged to the catheter shaft 144 at an area adjacent to the balloon 114.

When the balloon is in the reduced state the sleeves 170 and 172 have sufficient radial strength to retain the ends of the balloon 114 in the folded and reduced profile configuration. By retaining the ends of the balloon 114 in the folded configuration, absent inflation of the balloon 114, the balloon will tend to remain folded or reduced. When the balloon 114 is inflated or otherwise expanded, the radially contractive force of first portion 178 of each sleeve is overcome by the outwardly acting force of the balloon's inflation thereby allowing the balloon to unfold or expand from the reduced state to the expanded state. In some embodiments the sleeves 170 and 172 may be configured to retract or otherwise substantially withdraw from the end portions 174 and 176 of the balloon 114.

The sleeves may be constructed from any of a variety of materials such as are described in U.S. Pat. No. 6,443,980; U.S. Pat. No. 6,221,097; U.S. Pat. No. 6,554,841; U.S. Pub. application No. 2002-0038140 A1; and U.S. Pub. application No. 2002-0038141 A1, the entire content of each of which are incorporated herein by reference.

In at least one embodiment, an example of which is shown in FIG. 21, the first portion 178 of each sleeve 170 and 172 may comprise a thickened region or lip 182 which provides the sleeves 170 and 172 with a raised profile of sufficiency to engage each end of the rotatable sheath 102. By providing the sleeves with lips 182 in this manner, the sleeves will act in a manner similar to that of the previously described locks by preventing pr reducing the potential longitudinal displacement of the sheath 102 and the entire assembly 100 relative to the balloon 114 and catheter 116.

One or more sleeves 170 and/or 172 with lips 182 may be used in conjunction with or as an alternative to locks 152 to aid in controlling and/or eliminating potential longitudinal displacement of the assembly 100 relative to the catheter 116.

In some embodiments, an example of which is shown in FIG. 23, an assembly 100 equipped catheter 116 is provided with a protector 190 that is disposed about the end portions 174 and 176 of the balloon 114, and in at least one embodiment, one or more adjacent portions of the catheter 116 such as the catheter tip 105. Protector 190 is intended to retain the balloon 114 in the reduced folded configuration prior to its removal before the system 300 is utilized in a delivery procedure. In some embodiments, an example of which is shown in FIG. 22, the protector 190 comprises a proximal housing portion 194, a distal housing portion 196 and an intermediate portion 198 extending therebetween.

In some embodiments the protector 190 may be a cylindrical member with one or both ends being substantially opened or closed. In at least one embodiment at least a portion of the protector, such as the proximal housing portion 194 defines a longitudinal opening or slit 200 which allows the proximal housing portion 196 to be slid on and around the proximal end portion 174 of the balloon 114 once the distal housing portion 196 is positioned about the proximal end portion 176 of the balloon 114 and/or the catheter tip 105. The protector 190 is removed by pulling the proximal housing portion 194 radially away from the balloon 114 along the slit 200 until the housing 194 is fully removed from about the balloon 114 and then moving the protector 190 in a more longitudinal direction to slide the distal housing portion 196 off of the end of the catheter.

In some embodiments the slit 200 may extend from the proximal housing portion 194 to other regions of the protector 190 including the distal housing portion 196.

In some embodiments the intermediate portion 198 is a single member of material running along side a portion of the external surface of the stent 120. However, in some embodiments the intermediate portion 190 may have a more substantially tubular configuration to provide increased coverage to the stent 120 and thus better protection from physical contact as well.

In some embodiments the catheter 116 is equipped with one or more sleeves 170 and 172 as well as protector 190 in combination.

The protector may be additionally configured and constructed of any suitable material such as is described in U.S. Pat. No. 5,893,868; U.S. Pat. No. 6,152,944; U.S. Pat. No. 6,416,529; U.S. Pat. No. 6,613,067; U.S. Pat. No. 6,132,450; U.S. Pub. application No. 2002-0116045-A1; and U.S. Pub. application No. 2002-0120320-A1, the entire contents of each of which being incorporated herein by reference.

In some embodiments one or more of the various elements described herein, such as including but not limited to: at least a portion of one or more of the catheter shaft 144, balloon 114, sheath 104, secondary lumen housing 104, lock(s) 152, rotating collar 150, sleeves 170 and 172, and stent 120 are at least partially constructed of a radiopaque material.

Turning now to FIG. 24, as it has been described thus far, the assembly 100 may be considered to include the rotating collar 150. Such an assembly 100 is thus freely rotatable about the catheter shaft 144, by way of collar 150, as well as rotatable about the balloon 114 of the catheter 116, by way of the rotatable sheath 102.

The system 300 described herein including the catheter 116, assembly 100 and stent 120 is utilized in a stent delivery procedure by being advanced along a primary guide wire 107 and the secondary guide wire 108, such as in the manner shown in FIG. 24. Before insertion of the system 300 into the vessel 199, the guide wires 107 and 108 are inserted into the vessel 199 and advanced therethough to a vessel bifuircation 203 whereat the primary guide wire 107 continues along the vessel 199 or primary vessel branch 205 and the secondary guide wire 108 is advanced in to a side branch vessel 207.

As has been previously described, the assembly 100 is advanced along the secondary guide wire 108 via the secondary guide wire lumen 106, which is defined by the secondary guide wire housing 104. The catheter 116 is advanced along the primary guide wire 107, which extends through a primary guide wire lumen 204 defined by the catheter shaft 144.

It is noted that in some embodiments the catheter shaft 144 also defines a primary inflation lumen 211 which is in fluid communication with the balloon 114 for inflation thereof. In some embodiments the primary inflation lumen 211 and the primary guide wire lumen 204 are one and the same within the confines of the shaft 144, but the primary inflation lumen 211 terminates within the balloon interior, while the primary guide wire lumen 204 extends through the balloon and out the catheter tip 105.

Because of the rotatability of the assembly 100 and associated stent 120 about the catheter 116, as the system 300 is simultaneously advanced along the guide wires 107 and 108, the assembly 100 and stent 120 will be rotated into a position which aligns the secondary opening of the stent 130a with the opening 209 of the side branch vessel 207 into which the secondary guide wire 108 extends. The capacity to rotate the assembly 100 and the associated stent 120 into position in this manner avoids the need to apply rotational torque to the catheter 116 as all rotational activity is provided by the rotating assembly 100 which will rotate according to the path established by the secondary guide wire 108 and more especially, according to the divergence of the path established by the secondary guide wire 108 and primary guide wire 107 shown in FIG. 24.

Once properly positioned at the bifurcation 203, the balloon 114 is inflated or otherwise expanded in the normal manner. When the balloon 114 is inflated, the expanding balloon 114 will engage the sheath 102, thereby interrupting the sheath's ability to rotate about the balloon 114 and ensuring an accurate deployment of the stent 120. It should be further noted that as the balloon 114 expands in diameter, so to does the sheath 102 thus allowing the stent 120 to be expanded and deployed into the vessel 199 as is shown in FIG. 24. Once the stent 120 is deployed the system is removed.

In some embodiments, the stent 120 may require additional expansion in order to better engage the wall 201 of the vessel 199. As such, as is shown in FIG. 26, one or more so-called "kissing" or seating balloons 210 and 212 may be advanced along the guide wires 107 and 108 and into the flow path of the stent 120 and expanded therein in order to more securely engage the stent 120 against the vessel wall 201. In some embodiments, it may be desired to provide the secondary opening 130a by the expanding balloon with an enlarged area. As such, one of the kissing balloons 210 and 212 maybe advanced through the secondary opening 130a. When the balloon is expanded therein, the force applied to the members 132 adjacent to the secondary opening 130a will tend to further distort the members 132 away from one another thereby enlarging the size of the secondary opening 130a.

As is shown in FIG. 27, by providing an enlarged secondary opening 130a to the stent 120, a secondary stent 121 may be advanced and/or deployed adjacent to, through, and/or or at least partially within the secondary opening 130a to provide complete stent support to the vessel bifurcation 203.

As indicated above the present invention is embodied in a variety of forms. In FIGS. 28 and 29 an alternative embodiment to the system 300 is shown wherein the rotatable sheath 102 is further disposed about the secondary guide wire housing 104, and is likewise rotatable thereabout. In order to accommodate such rotatability the sheath 102 defines a secondary sheath opening 131 through which the secondary guide wire housing 104 is passed.

As indicated above, in some embodiments, an example of which is shown in FIG. 28 the secondary guide wire housing 104 may be passed at least partially through the collar 150, and/or the collar 150 may define a lumen 151 through which the secondary guide wire 108 and/or housing 104 may be passed before entering into the secondary guide wire housing 104.

In yet another embodiment, an example of which is shown in FIG. 30, the system 300 comprises a primary balloon 114 and a secondary balloon 115. In this embodiment one or more of the guide wire lumens may also act as an inflation lumen or the guide wire lumens and inflation lumens may be distinct. Because the secondary balloon 115 is external to the sheath 102, the sheath 102, stent 120 and secondary balloon 115 are all rotatable about the primary balloon 114 prior to expansion thereof However, given the desire to have a minimum excess of length in the secondary lumen housing 104, the secondary balloon 115 will typically be limited in its ability to rotate about the primary balloon 114 to at most two full rotations 720 degrees. In some embodiments rotation will be limited to a single full rotation or 360 degrees.

Because the system employs two balloons, the use of kissing balloons as previously described may be avoided.

In another embodiment shown in FIG. 31, the system 300 shown also employs a two balloon configuration. In this case the catheter shaft 144 defines a primary guide wire lumen 204 which also defines a primary inflation lumen 211 which is in fluid communication with the balloon 114, such as in the manner previously described. Running adjacent to the shaft 144 is a proximal secondary inflation lumen housing 213, which defines a proximal secondary inflation lumen 215 which terminates at the collar 150 and is in fluid communication therewith. In some embodiments the proximal secondary inflation lumen 215 and the primary inflation lumen 211 may be a common lumen or separate lumens contained within the shaft 144.

In the embodiments shown in FIG. 31, the collar 150 comprises two portions: a collar housing 220 and a rotatable portion 222 at least partially contained within the housing 220 and rotatable relative thereto. As is shown, the shaft 116, along with the primary inflation lumen 211 and primary guide wire lumen 204, extends through the collar 150. The rotatable portion 222 rotates freely about the shaft 144 when the collar 150 is in the unsealed state, which is discussed in greater detail as follows.

The collar housing 220 defines a fluid directing chamber 224 which is in fluid communication with the proximal secondary inflation lumen 215. When the secondary balloon 115 is inflated, an inflation fluid, indicated by arrow 226, is transported along the proximal secondary inflation lumen 215 and into the fluid directing chamber 224. The pressure caused by the fluid 226 passing into the chamber 224, or some other/additional activating mechanism or trigger, activates a sealing mechanism 230 between the housing 220 and the rotatable portion 222. Activation of the sealing mechanism 230 places the collar 150 in a sealed state wherein the rotatable portion 222 is no longer capable of freely rotating relative to the housing 220 and/or the catheter shaft 144. In addition, once the collar 150 is in the sealed state, the fluid 226 will move into the distal secondary inflation lumen 228 of the distal secondary inflation lumen housing 231 which is in fluid communication with the fluid directing chamber 224 via the rotating portion 222 as well as the secondary balloon 115.

In at least one embodiment the distal secondary inflation lumen housing 231 defines a sealed port 232 through which the secondary guide wire housing 104 may enter the lumen 228 and pass through the secondary balloon 115, in the manner shown in FIG. 31. As shown in FIG. 32 however, in some embodiments the secondary guide wire housing 104 and associated secondary guide wire lumen 106 may be externally adjacent to the distal secondary inflation lumen housing 231. By providing the secondary balloon 115 with a separate inflation lumen 228 and guide wire lumen 106 the use of a sealed port in the distal secondary inflation lumen housing may be avoided.

In some embodiments one or more of the various portions of the catheter shafts, lumens and housings may be provided with a substantially crescent shape to provide the overall system 300 with the lowest possible profile. An example of such a provision is shown in FIG. 32 wherein the distal secondary inflation lumen housing 231 has a substantially crescent shaped cross-section. As a result of this the housing 231 may be in a more intimate contact with the catheter shaft and/or rotatable sheath as the system 300 is advanced through the tortuous confines of the vasculature.

As discussed above, in reference to the embodiment shown in FIG. 31, where the system 300 employs two balloons 114 and 115 on a single catheter assembly, the collar 150 includes a sealing mechanism 230 which is actuatable to provide the collar 150, and more particularly the interface of the housing 220 and the rotatable portion 222, with a sealed state, wherein inflation fluid 226 may be passed from the fluid directing chamber 224, through the rotating portion 222 and eventually to the secondary balloon 115; and an unsealed state wherein the rotatable portion 222 remains free to rotate within and/or adjacent to the housing 220.

A first embodiment of a sealing mechanism 230 is shown in FIGS. 33 and 34. In this embodiment the collar 150 employs a shape memory collar or ring 240 which is in conductive communication with at least one conducting wire, sleeve or member 242. When the collar 150 is in the unsealed state, such as is shown in FIG. 33, the rotating portion 222 and the ring 240 are spaced apart to allow free rotation of the rotating portion 222 within the housing 220. When the ring 240 is actuated by a conductive signal, indicated by arrow 244 shown in FIG. 34, the ring 240 will expand or otherwise alter its configuration to attain a preprogrammed state which causes the ring 240 or portion thereof, to extend radially inward to engage the rotating portion 222, thereby sealing the rotating portion 222 against the housing 220. As a result fluid 226 is now free to flow through and from the fluid directing chamber 224, through the now immobilized rotatable portion 222 and on through the distal secondary inflation lumen 228 and the secondary balloon.

The ring 240 may be any sort of shape memory material or materials desired, such as nitinol, shape memory polymer, etc. As such, the ring 240 may be actuated by any sort of conductive signal 244 which is known to cause a shape memory material to transform from a first state to a preprogrammed second state.

Another embodiment of a sealing mechanism 230 is shown in FIGS. 35 and 36. In this embodiment the rotatable portion 222 defines one or more expandable inflation chambers 250 which are in fluid communication with the fluid directing chamber 224. When fluid 226 is injected into the fluid directing chamber 224, the fluid will enter one or more inflation chamber ports 252 which will allow the fluid 226 to fill the chambers 250 from an unexpanded and unsealed state shown in FIG. 35 to an expanded and sealed state shown in FIG. 36. In the unsealed state, the rotation of the rotatable portion 222 remains unimpeded by the reduced diameter of the unexpanded chambers 250. When the chambers 250 are expanded by fluid 226, the rotatable portion 222 becomes engaged to the housing 220 via the greater diameter of the expanded chambers 250. Once the collar 150 is placed in the sealed state in this manner the fluid 226 is free to pass through the rotatable portion 222 and on through the distal secondary inflation lumen 228.

The invention has been described with reference to the embodiments. Obviously, modifications and alterations will occur to others upon a reading and understanding of this specification. For example, the illustrated embodiments use a balloon to expand the stent although, as briefly noted above, a self expanding, self deploying or hybrid expandable stent can be used without departing from the features of the present invention. The invention is intended to include all such modifications and alterations thereof.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
a catheter, the catheter comprising a catheter shaft, the catheter shaft defining a first guide wire lumen for passage of a first guide wire therethrough;
a rotatable sheath, the rotatable sheath extending around an exterior of at least a portion of the catheter shaft and rotatable relative to the catheter shaft at a position radially outward from the catheter shaft, the rotatable sheath having a length substantially less than that of the catheter shaft;
a secondary guide wire housing, the secondary guide wire housing defining a secondary guide wire lumen for passage of a secondary guide wire therethrough, at least a first distal portion of the guide wire housing in contact with at least a first proximal portion of the rotatable sheath; and
a stent, the stent being expandable from a reduced stent state to an expanded stent state, and defining a flow path between a proximal end opening and a distal end opening, the stent being at least partially constructed from a plurality of interconnected stent members that define a plurality of cell openings therebetween, each of the cell openings being in fluid communication with the flow path, in the reduced stent state the stent is positioned radially outward from and extends around an exterior of at least a portion of the rotatable sheath and at least a portion of the secondary guide wire housing, a distal end portion of the secondary guide wire housing exiting the flow path of the stent through one of the plurality of cell openings.

2. The assembly of claim 1 wherein the stent is selected from at least one member of the group consisting of: a self-expanding stent, a balloon-expandable stent, a hybrid expandable stent and any combination thereof.

3. The assembly of claim 1 wherein at least a portion of the stent is coated with at least one therapeutic agent.

4. The assembly of claim 3 wherein the at least one therapeutic agent is at least one non-genetic therapeutic agent selected from at least one member of the group consisting of: anti-thrombogenic agents; anti-proliferative agents; anti-inflammatory agents; antineoplastic agents; anti-miotic agents; anesthetic agents; anti-coagulants; vascular cell growth promoters; vascular cell growth inhibitors; bifunctional molecules consisting of an antibody and a cytotoxin; cholesterol-lowering agents; vasodilating agents; and agents which interfere with endogenous vascoactive mechanisms.

5. The assembly of claim 3 wherein the at least one therapeutic agent is at least one genetic therapeutic agent selected from at least one member of the group consisting of: anti-sense DNA and RNA; DNA coding for anti-sense RNA, tRNA or rRNA to replace defective or deficient endogenous molecules; angiogenic factors including growth factors; cell cycle inhibitors including CD inhibitors, thymidine kinase ("TK") and other agents useful for interfering with cell proliferation; at least one of the family of bone morphogenic proteins ("BMP's"); dimeric proteins; and molecules capable of inducing an upstream or downstream effect of a BMP, "hedgehog" proteins, or the DNA's encoding them.

6. The assembly of claim 3 wherein the at least one therapeutic agent comprises at least one polymer coating, the at least one coating selected from at least one member of the group consisting of: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers including EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions; polycsaccharides; hyaluronic acid; squalene emulsions; polyacrylic acid, a copolymer of polylactic acid and polycaprolactone; medical-grade biodegradable materials; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules including chitosan and Hydroxylpropylmethylcellulose; surface erodible material; maleic anhydride copolymers; zinc-calcium phosphate; amorphous polyanhydrides; sugar; carbohydrate biodegradable polymers; and polymers dissolvable in bodily fluids; A block copolymers; and B block copolymers.

7. The assembly of claim 5 wherein the at least one therapeutic agent is a growth factor selected from at least one member of the group consisting of: acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor.

8. The assembly of claim 5 wherein the at least one therapeutic agent is a bone morphogenic proteins ("BMP's") selected from at least one member of the group consisting of: BMP-2, BMP-3, BMP-4, BMP-5, BMP-6 (Vgr-1), BMP-7

(OP-1), BMP-8, BMP-9, BMP-10, BMP-11, BMP-12, BMP-13, BMP-14, BMP-15, and BMP-16.

9. The assembly of claim 5 wherein the at least one therapeutic agent comprises a dimeric protein selected from at least one member of the group consisting of: homodimers and heterodimers.

10. The assembly of claim 6 wherein the at least one therapeutic agent comprises at least one coating from polymer dispersion selected from at least one member of the group consisting of polyurethane dispersions, fibrin, collagen and derivatives thereof.

11. The assembly of claim 6 wherein the at least one therapeutic agent comprises at least one polysaccharide selected from at least one member of the group consisting of: celluloses, starches, dextrans, alginates, and derivatives.

12. The assembly of claim 6 wherein the at least one therapeutic agent comprises a medical-grade biodegradable material selected from at least one member of the group consisting of: PGA-TMC, Tyrosine-Derived Polycarbonates, and arylates.

13. The assembly of claim 4 wherein the at least one therapeutic agent comprises a anti-thrombogenic agent selected from at least one member of the group consisting of: heparin, heparin derivatives, urokinase, and PPack (dextrophenylalanine proline arginine chloromethylketone).

14. The assembly of claim 4 wherein the at least one therapeutic agent comprises an anti-proliferative agent selected from at least one member of the group consisting of: enoxaprin, angiopeptin, monoclonal antibodies capable of blocking smooth muscle cell proliferation, hirudin, and acetylsalicylic acid.

15. The assembly of claim 7 wherein the at least one therapeutic agent comprises an anti-inflammatory agents selected from at least one member of the group consisting of: dexamethasone, prednisolone, corticosterone, budesonide, estrogen, sulfasalazine, and mesalamine.

16. The assembly of claim 4 wherein the at least one therapeutic agent comprises an anti-coagulants selected from at least one member of the group consisting of: D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides.

17. The assembly of claim 4 wherein the at least one therapeutic agent comprises at least one member of the group consisting of: paclitaxel, 5-fluorouracil, cisplatin, vinblastine, vincristine, epothilones, endostatin, angiostatin, and thymidine kinase inhibitors.

18. The assembly of claim 4 wherein the at least one therapeutic agent comprises an anesthetic agent selected from at least one member of the group consisting of: lidocaine, bupivacaine, and ropivacaine.

19. The assembly of claim 4 wherein the at least one therapeutic agent comprises a vascular cell growth promoters selected from at least one member of the group consisting of: growth factor inhibitors, growth factor receptor antagonists, transcriptional activators, and translational promoters.

20. The assembly of claim 4 wherein the at least one therapeutic agent comprises a vascular cell growth inhibitors selected from at least one member of the group consisting of: growth factor inhibitors, growth factor receptor antagonists, transcriptional repressors, translational repressors, replication inhibitors, inhibitory antibodies, antibodies directed against growth factors, and bifunctional molecules consisting of a growth factor and a cytotoxin.

21. A catheter assembly comprising:
a catheter, the catheter comprising a catheter shaft, the catheter shaft defining a first guide wire lumen for passage of a first guide wire therethrough;
a rotatable sheath, the rotatable sheath being disposed about at least a portion of the catheter shaft and rotatable about and relative to the catheter shaft, the rotatable sheath having a length substantially less than that of the catheter shaft;
a secondary guide wire housing, the secondary guide wire housing defining a secondary guide wire lumen for passage of a secondary guide wire therethrough, at least a first distal portion of the guide wire housing being engaged to at least a first proximal portion of the rotatable sheath; and
a stent, the stent being expandable from a reduced stent state to an expanded stent state, and defining a flow path between a proximal end opening and a distal end opening, the stent being at least partially constructed from a plurality of interconnected stent members that define a plurality of cell openings therebetween, each of the cell openings being in fluid communication with the flow path, in the reduced stent state the stent is disposed about at least a portion of the rotatable sheath and at least a portion of the secondary guide wire housing, a distal end portion of the secondary guide wire housing exiting the flow path of the stent through one of the plurality of cell openings,
at least a portion of the stent is coated with at least one therapeutic agent,
the at least one therapeutic agent is at least one type of cellular material selected from at least one member of the group consisting of: autologous cells of human origin; allogeneic cells of human origin; and xenogeneic cells of non-human origin.

22. The assembly of claim 21 wherein the cellular material is selected from at least one member of the group consisting of: side population cells; lineage negative cells; lineage negative CD34$^-$ cells; lineage negative CD34$^+$ cells; lineage negative $^-$cKit$^+$ cells; mesenchymal stem cells; cord blood bells; tissue derived stem cells; whole bone marrow; bone marrow mononuclear cells; endothelial progenitor cells; satellite cells; muscle derived cells; go cells; endothelial cells; adult cardiomyocytes; fibroblasts; smooth muscle cells; cultures of mesenchymal stem cells with 5-aza forces differentiation into cardiomyocytes; adult cardiac fibroblasts +5-aza; genetically modified cells; tissue engineered grafts; MyoD scar fibroblasts; Pacing cells; embryonic stem cell clones; embryonic stem cells; fetal or neonatal cells; immunologically masked cells; tissue engineered grafts; genetically modified cells; and teratoma derived cells.

23. The assembly of claim 22 wherein the wherein the cellular material includes tissue derived stem cells including cardiac derived stem cells.

24. A catheter assembly comprising:
a catheter, the catheter comprising a catheter shaft, the catheter shaft defining a first guide wire lumen for passage of a first guide wire therethrough;
a rotatable sheath, the rotatable sheath being disposed about at least a portion of the catheter shaft and rotatable about the catheter shaft, the rotatable sheath having a length substantially less than that of the catheter shaft and being rotatably disposed about at least a portion of a medical balloon;
a secondary guide wire housing, the secondary guide wire housing defining a secondary guide wire lumen for passage of a secondary guide wire therethrough, at least a first distal portion of the guide wire housing being engaged to at least a first proximal portion of the rotatable sheath;

the medical balloon fixedly mounted to the catheter shaft, the medical balloon expandable from a reduced configuration to an expanded configuration, the catheter shaft further defining an inflation lumen, the inflation lumen being in fluid communication with the medical balloon; and a rotatable collar, the rotatable collar rotatably disposed about a portion of the catheter shaft proximal of the medical balloon, at least a first proximal portion of the secondary guide wire housing being engaged to at least a portion of the rotatable collar.

25. The assembly of claim 24 wherein the rotatable collar defines a catheter shaft lumen therethrough, the catheter shaft being positioned with in the catheter shaft lumen, the catheter shaft lumen having a diameter greater than an outer diameter of the catheter shaft.

* * * * *

UNITED STATES PATENT AND TRADEMARK OFFICE
CERTIFICATE OF CORRECTION

| | | |
|---|---|---|
| PATENT NO. | : 7,314,480 B2 | Page 1 of 1 |
| APPLICATION NO. | : 10/657472 | |
| DATED | : January 1, 2008 | |
| INVENTOR(S) | : Eidenschink et al. | |

It is certified that error appears in the above-identified patent and that said Letters Patent is hereby corrected as shown below:

Title page, (63) Related U.S. Application Data: "Feb. 27, 2002." should read --Feb. 27, 2003.--

Col. 1, line 18: "DESCRIPTION OF THE RELATED ART" should read --Description of the Related Art--

Col. 11, line 48: "The TECOPHIL® C sheath" should read --The TECOPHLIC® sheath--

Col. 27, line 32, claim 15: "claim 7 wherein" should read --claim 4 wherein--

Col. 28, line 40, claim 22: "blood bells tissue" should read --blood cells tissue--

Signed and Sealed this

Twenty-sixth Day of August, 2008

JON W. DUDAS
*Director of the United States Patent and Trademark Office*